(12) United States Patent
Gagnoni et al.

(10) Patent No.: US 10,155,740 B2
(45) Date of Patent: Dec. 18, 2018

(54) CRYSTAL FORMS OF IMMUNOMODULATORY DRUG POMALIDOMIDE AND CO-CRYSTAL WITH GENTISIC ACID

(71) Applicant: F.I.S.—FABBRICA ITALIANA SINTETICI S.P.A., Montecchio Maggiore (VI) (IT)

(72) Inventors: Alessandro Gagnoni, Luino Varese (IT); Antonio Germani, Lugano (CH); Nicolas Tesson, L'Hospitalet de Llobregat (ES)

(73) Assignee: F.I.S.—FABBRICA ITALIANA SINTETICI S.P.A, Montecchio Maggiore (VI) (IT)

( * ) Notice: Subject to any disclaimer, the term of this patent is extended or adjusted under 35 U.S.C. 154(b) by 0 days.

(21) Appl. No.: 15/560,723

(22) PCT Filed: Nov. 24, 2016

(86) PCT No.: PCT/EP2016/078726
§ 371 (c)(1),
(2) Date: Sep. 22, 2017

(87) PCT Pub. No.: WO2017/121530
PCT Pub. Date: Jul. 20, 2017

(65) Prior Publication Data
US 2018/0099944 A1    Apr. 12, 2018

(30) Foreign Application Priority Data
Jan. 14, 2016  (IT) ............... UB2016A9994

(51) Int. Cl.
*C07D 401/04*  (2006.01)
*A61P 35/00*   (2006.01)

(52) U.S. Cl.
CPC ............ *C07D 401/04* (2013.01); *A61P 35/00* (2018.01); *C07B 2200/13* (2013.01)

(58) Field of Classification Search
CPC .................................................. C07D 401/04
See application file for complete search history.

(56) References Cited

FOREIGN PATENT DOCUMENTS

| CN | 103275062 A | * | 9/2013 |
|----|-------------|---|--------|
| CN | 103275062 A |   | 9/2013 |
| CN | 103288797 A |   | 9/2013 |
| CN | 103626738 A |   | 3/2014 |
| WO | 2007005972 A1 | | 1/2007 |
| WO | 2011050962 A1 | | 5/2011 |
| WO | 2013126326 A1 | | 8/2013 |
| WO | 2014160690 A1 | | 10/2014 |
| WO | 2014170909 A2 | | 10/2014 |

OTHER PUBLICATIONS

Chanan-Khan "Pomalidomide: the new immunomodulatory agent for the treatment of multiple myeloma" Blood Cancer Journal ( 2013) 3, e143, 1-7.*
Katritzky "Perspective on the Relationship between Melting Points and Chemical Structure" Crystal Growth & Design, vol. 1, No. 4, 2001 261-265, pp. 261-262.*
International Search Report and Written Opinion for International Application No. PCT/EP2016/078726 (dated Jan. 18, 2017) (11 Pages).

* cited by examiner

*Primary Examiner* — David K O'Dell
(74) *Attorney, Agent, or Firm* — Lucas & Mercanti LLP

(57) ABSTRACT

The present invention relates to novel solid crystal forms of Pomalidomide named Form B, Form M, Pomalidomide: Gentisic acid co-crystal and their preparation. Advantageously, these solid forms are used in pharmaceutical compositions for the treatment and the prevention of multiple myeloma, of inflammatory diseases, of autoimmune diseases, of immune diseases, of myelodysplastic syndrome, of myeloproliferative disorders, of anemia, of scleroderma, amyloidosis or of other diseases associated with unwanted angiogenesis.

17 Claims, 16 Drawing Sheets

CRYSTAL FORMS OF IMMUNOMODULATORY DRUG POMALIDOMIDE AND CO-CRYSTAL WITH GENTISIC ACID

CROSS-REFERENCE TO RELATED APPLICATIONS

This application is a 371 of PCT/EP2016/078726, filed Nov. 24, 2016, which claims the benefit of Italian Application No. UB2016A009994, filed Jan. 14, 2016.

FIELD OF THE INVENTION

The present invention relates to new solid forms of Pomalidomide, in particular to a new co-crystal, stable, easily purifiable and more water-soluble than Pomalidomide, and to processes for its preparation.

STATE OF THE ART

Pomalidomide or (R,S)-4-Amino-2-(2,6-dioxo-3-piperidinyl)-isoindol-1,3-dione (CAS n. 19171-19-8) of formula I:

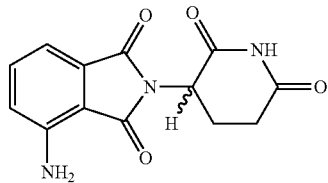

is a drug analogous to thalidomide, active as anti-inflammatory, immunomodulator, anti-tumor and anti-angiogenic, particularly indicated for the treatment of multiple myeloma.

The preparation of the racemic Pomalidomide has been described in the WO2007005972A1 patent application in the name of Celgene Corporation.

In example 3 of this patent application, the product precipitates from the acetonitrile used in the reaction as yellow solid crystal (HPLC purity 99.57%), with melting point 315.5-317.5° C.

In example 17 the precipitation of Pomalidomide from DMSO/water is described: the solid so obtained has a melting point of 321-323° C. (herein below Form O). This method would appear, however, not very effective in removing impurities, as evidenced by HPLC analyses carried out on samples of Pomalidomide obtained from the crude by precipitation from DMSO/water in patent applications CN103288797A and CN103275062A.

The patent application WO2014170909A2, describes some methods of preparation of crystal form I and a purification process of Pomalidomide.

The patent application WO2013126326A1 describes the preparation and characterization of a Pomalidomide crystal form named Form A.

There, in particular, form A is obtained by crystallization from acetonitrile, methyl ethyl ketone, tetrahydrofuran (Table 4) nitromethane (par. 00232), and by means of suspension in acetonitrile, water or mixtures thereof, (par. 00233-00236), and mainly characterized by DSC, TGA and XRPD (FIG. 1-17 of the WO2013126326A1 application).

Pomalidomide currently on the market is generally obtained by precipitation from DMSO/water and it appears as a non-hygroscopic crystalline yellow powder, characterized by a very low solubility in water.

In this regard, at pages 10 and 11 of the document of the European Medicines Agency Pomalidomide Celgene Assessment Report (EMA/CHMP/427059/2013) it is stated that: " . . . the active substance . . . is slightly soluble in acetone, acetonitrile, methylene chloride, methyl ethyl ketone, and THF, very slightly soluble in absolute ethanol, ethyl acetate, heptane, methanol, 2-propanol and toluene, and practically insoluble in water".

In the WO2013126326A1 description in paragraph 00219 and in table 3, data are reported of the solubility of Pomalidomide in various solvents, including water. The compound is confirmed to have a very low solubility in this solvent (<1 mg/ml).

According to the International Classification System Biopharmaceutics Classification System (BCS) (http://www.fda.gov/AboutFDA/CentersOffices/OfficeofMedical-ProductsandTobacco/CDER/ucm128219.htm) of the US FDA (Food and Drug Administration), Pomalidomide is a compound of class IV, which has low solubility and permeability. The compounds of this class have generally poor bioavailability and are usually absorbed poorly and variably at the level of the intestinal mucosa.

In the document FDA CEDER—Appl. No 204026Orig1s000 Clinical Pharmacology and biopharmaceutics review, page 24 (available also on the Internet at the page http://www.accessdata.fda.gov/drugsatfda_docs/nda/2013/204026Orig1s000MedR.pdf page) it is stated that Pomalidomide at a dose of 2 mg is soluble in 250 ml of aqueous medium at pH 1.2, 4.5 and 6.8 but the clinical dose of 4 mg is not. From the saturation solubility data there reported in Table 13, and here collected in the following table 1 it is evident that the dissolution of Pomalidomide does not significantly improve even by changing the pH of the solution:

TABLE 1

Saturation solubility in aqueous medium as a function of pH at 37° C.

| Theoretical pH (Buffered Solution) | Pomalidomide solubility after 24 hours (μg/ml) |
|---|---|
| 1.2 (0.05N HCl) | 15.0 |
| 4.5 (0.05M acetato) | 14.6 |
| 6.8 (0.05M fosfato) | 13.2 | as further confirmation of the low tendency of Pomalidomide to dissolution in the aqueous medium. The poor water solubility of Pomalidomide limits the oral bioavailability of the substance, especially at the highest dosages.

Therefore, in this field, the need is particularly long-felt to increase the water solubility of Pomalidomide.

However improvement of the solubility by salification is not feasible since the molecule has no easily salifiable functional groups, except with very strong acids or bases, not always pharmaceutically acceptable. In this regard, to the best of our knowledge, in the literature very few salts of Pomalidomide are described and only with strong acids.

In the patent application WO2011050962A1 acid addition salts of Pomalidomide are claimed with generic HX acids having a pKa (at 25° C. in water) from −10 to +4, in particular the hydrochloride, the sulfate (pKa<1) and the acid sulfate (pKa=1.92). In the description, only Pomalidomide hydrochloride is specifically mentioned, in the formulation of Example 5, but its preparation is not described and no characterization is given especially in terms of solubility and stability. Furthermore in this patent application no specific examples are given or cited of another salt, and no data on their solubility in water.

In conclusion, as far as we know, to date no solid form of Pomalidomide is really available, that is more soluble than the known forms.

Instead it would be desirable to have more water-soluble solid forms available of Pomalidomide, of higher and constant in vivo absorption even at the highest clinical doses, which are stable, not hygroscopic, and can be prepared through simple processes and with high purity.

SUMMARY OF THE INVENTION

The Applicant has surprisingly found new solid forms of Pomalidomide that respond to the previously discussed needs of the field, improved water solubility, stability, ease of preparation and purity.

Therefore, a first aspect of the present invention is a new solid crystal form of Pomalidomide chosen between Form B, Form M and the co-crystal of Pomalidomide and Gentisic acid.

A second aspect of the present invention is a process for the preparation of a co-crystal of Pomalidomide and Gentisic acid in accordance with the first aspect of the present invention, which comprises a) providing Pomalidomide in a predetermined amount;

b) providing Gentisic acid in a molar ratio of not more than 4:1, than 3:1, than 2:1, than 1.5:1 or than 1.2:1 with respect to Pomalidomide;

c) contacting Pomalidomide and Gentisic acid and, optionally, at least one co-crystal Pomalidomide:Gentisic acid:
  c1) in solution or in suspension, in a suitable solvent, or
  c2) by grinding, optionally in the presence of traces of an appropriate solvent, d) maintaining in contact Pomalidomide and Gentisic acid for the time necessary to form the co-crystal in accordance with the first aspect of the present invention, and optionally e) separating the co-crystal from the solvent.

A third aspect of the present invention is a pharmaceutical composition comprising a therapeutically effective amount of a solid crystal form of Pomalidomide chosen between Form B, Form M, a co-crystal of Pomalidomide and Gentisic acid and their mixtures in accordance with the first aspect of the present invention and at least one pharmaceutically acceptable excipient.

A fourth aspect of the present invention is a solid crystal form of Pomalidomide chosen between Form B, Form M, a co-crystal of Pomalidomide and Gentisic acid and their mixtures, in accordance with the first aspect of the present invention, for use as a medication.

A fifth aspect of the present invention is a solid crystal form of Pomalidomide chosen between Form B, Form M, a co-crystal of Pomalidomide and Gentisic acid and their mixtures, in accordance with the first aspect of the present invention, for use in the prevention and treatment of multiple myeloma, of inflammatory diseases, of autoimmune diseases, of immune diseases, of myelodysplastic syndrome, myeloproliferative disorders, of anemia, of scleroderma, of amyloidosis or other diseases associated with unwanted angiogenesis.

A sixth aspect of the present invention is a process for the purification of crude Pomalidomide which comprises a) providing crude Pomalidomide in a predetermined amount;

b) providing Gentisic acid in a molar ratio of not more than 4:1, than 3:1, than 2:1, than 1.5:1 or than 1.2:1, with respect to Pomalidomide;

c1) contacting the crude Pomalidomide and Gentisic acid in solution or in suspension in a suitable solvent, optionally in the presence of at least one co-crystal of Pomalidomide:Gentisic acid;

d) maintaining in contact Pomalidomide and Gentisic acid for the time necessary to form the co-crystal in accordance with the first aspect of the present invention, e) separating the obtained co-crystal from the solvent, f) optionally crystallizing the co-crystal from an appropriate solvent, and g) recovering purified Pomalidomide from the co-crystal, preferably by suspension in an appropriate solvent.

DEFINITIONS

The term Pomalidomide generally refers to both the racemic form and the single R or S enantiomers, preferably to the racemic form.

In the pharmaceutical context, the term co-crystal refers to a solid crystal form comprising in the crystal lattice an active ingredient (API) and at least one other compound, named co-former. The co-former may be pharmacologically active or inactive. Unlike the salts, where the components are present in ionized state in the crystal lattice, in co-crystals the components are generally in the neutral state and interact through reversible weak non-ionic and non-covalent interactions. The API acronym means Active Pharmaceutical Ingredient, i.e. the active substance with pharmacological activity.

The term XRPD refers to X-Ray Powder Diffraction.

The term DSC refers to Differential Scanning calorimetry.

The 1H-NMR refers to Nuclear Magnetic Resonance spectroscopy of the proton.

The term TGA refers to Thermogravimetric Analysis.

A "therapeutically effective amount" refers to an amount of active ingredient sufficient to treat, alleviate and/or prevent a disease or disorder, and can be determined by the expert in the field through routine experimentation.

DETAILED DESCRIPTION OF THE INVENTION

A first aspect of the present invention is a new solid crystal form of Pomalidomide chosen between Form B, Form M, and a co-crystal of Pomalidomide and Gentisic acid.

Figure 1:
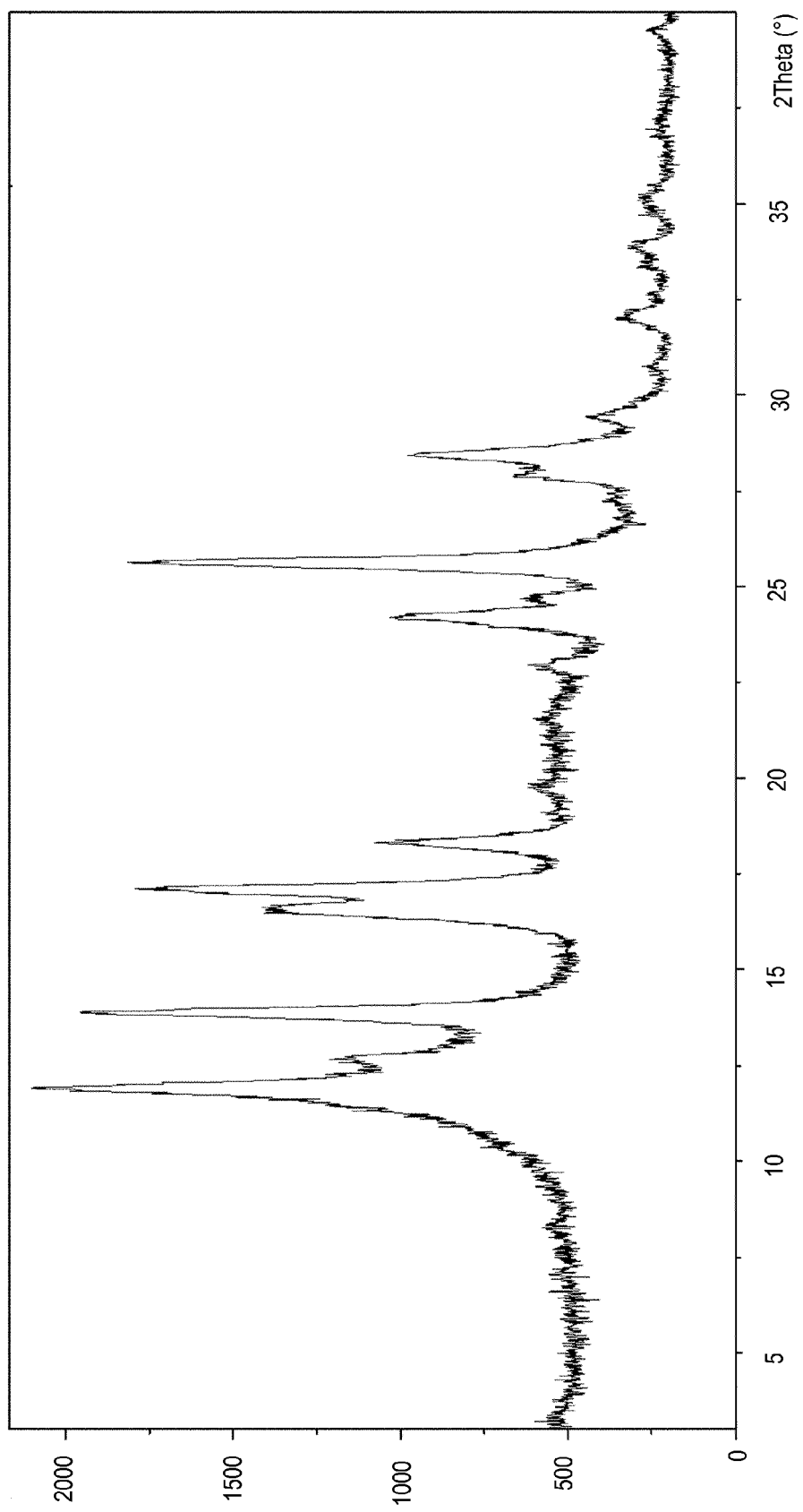
FIG. 1 is an XRPD diffractogram of the new form B of Pomalidomide.
Figure 2:
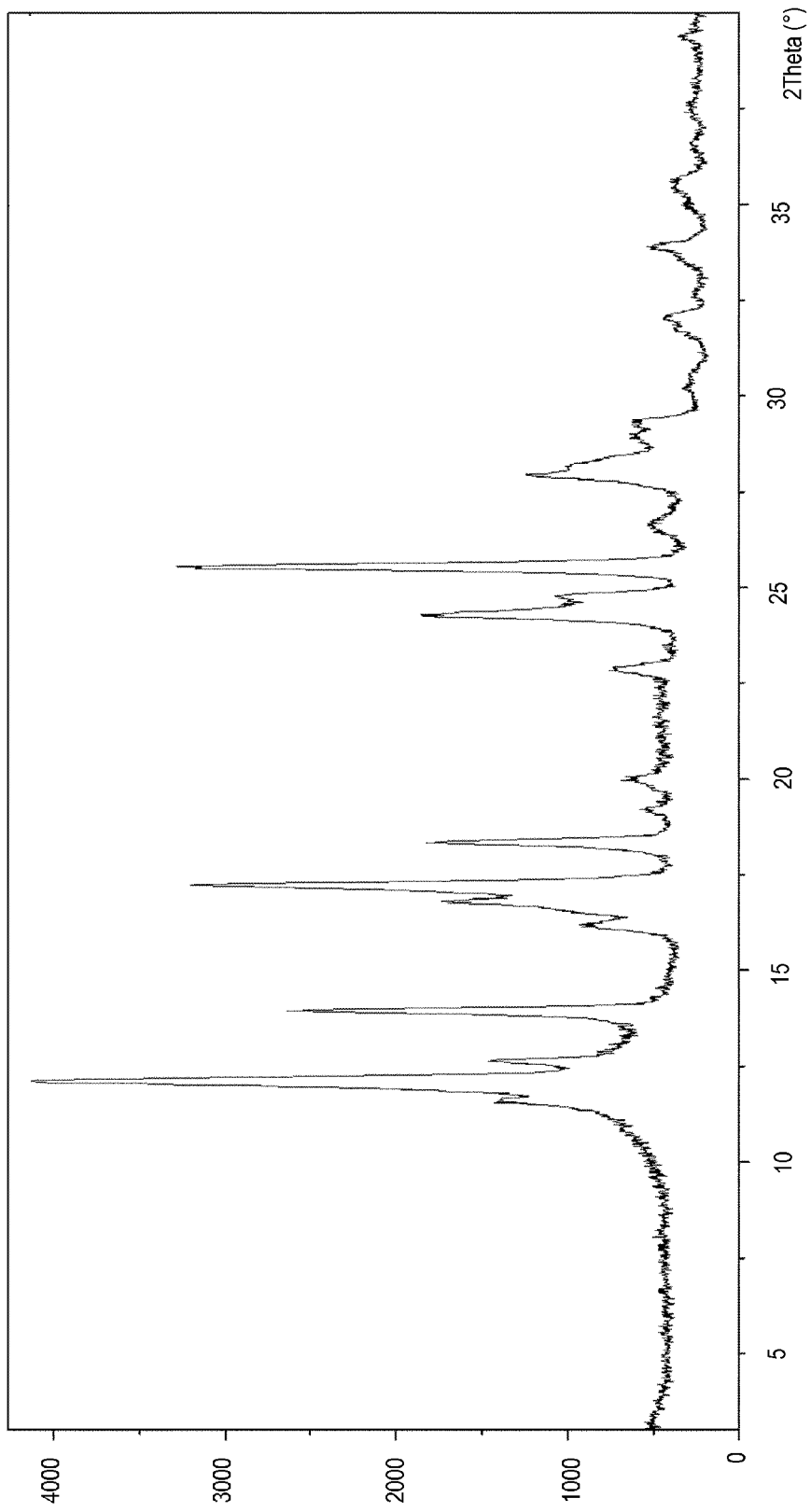
FIG. 2 is an XRPD diffractogram of the new form M of Pomalidomide.

The solid crystal forms B and M of Pomalidomide (Form B and Form M) are characterized by diffractograms XRPD shown in FIGS. 1 and 2 respectively.

The crystal form of Pomalidomide, named Form B, can be prepared by grinding the form O in the presence of chloroform or also, having already the crystals, by seeding with these during the grinding of the form O in the presence of tetrahydrofuran or isopropanol (grinding).

The crystal form of Pomalidomide, named Form M, can be prepared by suspension of the form O under stirring for a night in isopropanol (slurrying) after seeding with Form B.

An alternative method for the preparation of Form M prescribes suspending the form O under stirring for four days (slurrying) in dioxane and seeding with Form A, as described in the present experimental part.

Pomalidomide Form M is advantageously a non-hygroscopic form, i.e. it does not absorb moisture after exposure to a 100% relative humidity for one night.

From the overlapping XRPD diffractograms of the known Forms 0 and A and of the two new Forms B and M of Pomalidomide, it is evident that these crystal forms are similar but distinguishable. In particular, there are small shifts of 2θ at around 12.0°, 16.6° and 17.2° which follow the sequence Form B<Form O<Form M<Form A, while in correspondence of the most intense peak at 25.6°, they appear in the reverse order.

On the basis of the results of the tests of preparation of the various forms by suspension in solvent described in the experimental part, it could be concluded that the Form M has a higher stability than both Form B and Form O.

A particularly preferred aspect of the present invention is a co-crystal of Pomalidomide and Gentisic acid.

To the best of the applicant's knowledge, co-crystals of Pomalidomide are not known.

On the contrary, co-crystals of Lenalidomide, an analogue of Pomalidomide of formula II, are described:

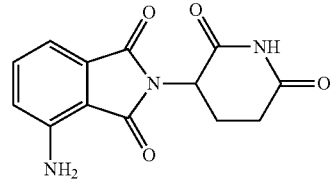

Pomalidomide

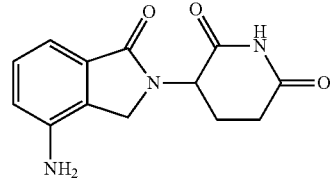

Lenalidomide in particular, co-crystals with urea (Crystal Growth & Design, 2014, 14 (6), pp 3069-3077 and WO2013012485A2), 3,5-dihydroxybenzoic acid (Crystal Growth & Design, 2014, 14 (6), pp 3069-3077), gallic acid, propyl gallate, oxalic acid, malonic acid, ammonium chloride and DL-tartaric acid (WO2013012485A2).

The above mentioned documents provide no suggestion on the choice of Gentisic acid as a co-former, neither for Lenalidomide nor for Pomalidomide, nor do they provide useful information to predict the properties of the possible co-crystal.

The Applicant has experimentally found (see Example 5, Table 6) that, despite the considerable structural similarity, the two APIs behave in a very different and not predictable way in the formation of co-crystals. In fact, the co-crystals preparation tests carried out with Pomalidomide and some co-formers of the Lenalidomide suggested by the above mentioned literature, particularly urea, oxalic acid, DL-tartaric acid and propyl gallate, have failed.

The Applicant has also tried co-formers structurally very close to Gentisic acid (III), in particular Vanillic acid (IV) and 2,4-dihydroxybenzoic acid (V):

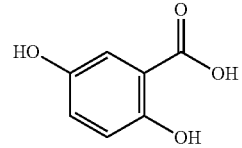

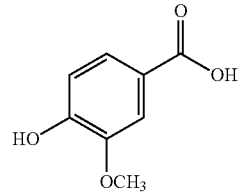

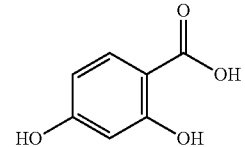

but without success, even seeding with the co-crystal of the present invention.

The Applicant has also tried to prepare co-crystals of Pomalidomide with several other co-formers not suggested in the above prior art, such as nicotinic acid, ascorbic acid, benzoic acid, pyridoxine, pyridoxine hydrochloride, L-pyroglutamic acid, L-malic acid, 4-aminobenzoic acid, L-proline, vanillin, glycolic acid, sorbic acid, betaine, cinnamic acid, L-glutamic acid, choline hydrochloride, maltol, formic acid, but always with negative results.

Unexpectedly, Gentisic acid or 2,5-dihydroxybenzoic acid, was the only co-former among those considered capable of forming co-crystals with Pomalidomide.

Gentisic acid is a weak organic acid (pKa=2.93 at 25° C.) very soluble in water. It's a metabolite of salicylic acid, which also has analgesic and anti-inflammatory properties, it is used in pharmaceutical preparations, for example as an antioxidant and stabilizer.

Pomalidomide is characterized by a pKa value of 11.61 calculated (corresponding to pKb=2.39). The difference in pK (pKb-pKa) between Pomalidomide and Gentisic acid is less than 1, meeting the requirements set forth by FDA guidelines in matter of co-crystals (also available on the Web at http://www.fda.gov/downloads/Drugs/ . . . /guidances/UCM281764.pdf). According to these guidelines, a complex in which substantially the proton transfer between the API and the co-former does not take place is considered a co-crystal, that is, when the difference in pKa between the pKb of the base and the pKa of the acid is less than 1.

Pomalidomide in the present co-crystal can be either in the racemic form, or in the single enantiomer form, or in mixtures thereof, preferably it is racemic Pomalidomide.

The co-crystal of the present invention comprises Pomalidomide and Gentisic acid in a molar ratio 1:1, as it is evidenced by the grinding preparation tests in the presence of excess Pomalidomide or Gentisic acid described in the experimental part and as it is confirmed by NMR analysis.

Figure 8:
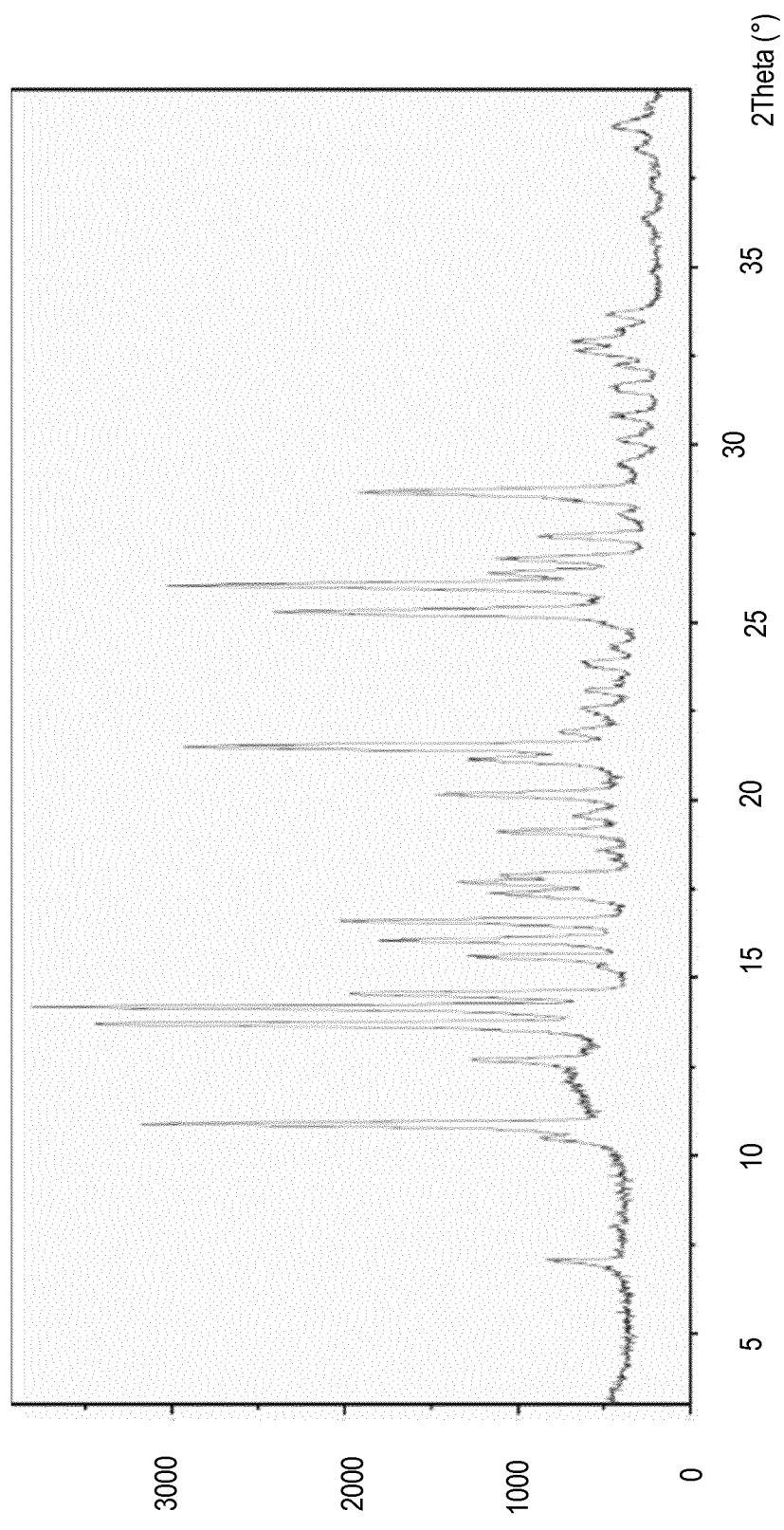
FIG. 8 is an XRPD diffractogram of the co-crystal of Pomalidomide and Gentisic acid Form 1 according to the invention.

The crystal form of the present co-crystal is here referred to as Form 1, it is characterized by an XRPD diffractogram which substantially corresponds to that shown in FIG. 8.

By the term "substantially corresponds" it is meant the indication that the values of 2θ(°) of the peaks in the XRPD diffractogram may vary not more than ±10%, preferably not more than ±5%, even more preferably not more than ±1% or ±0.5%.

Figure 7:
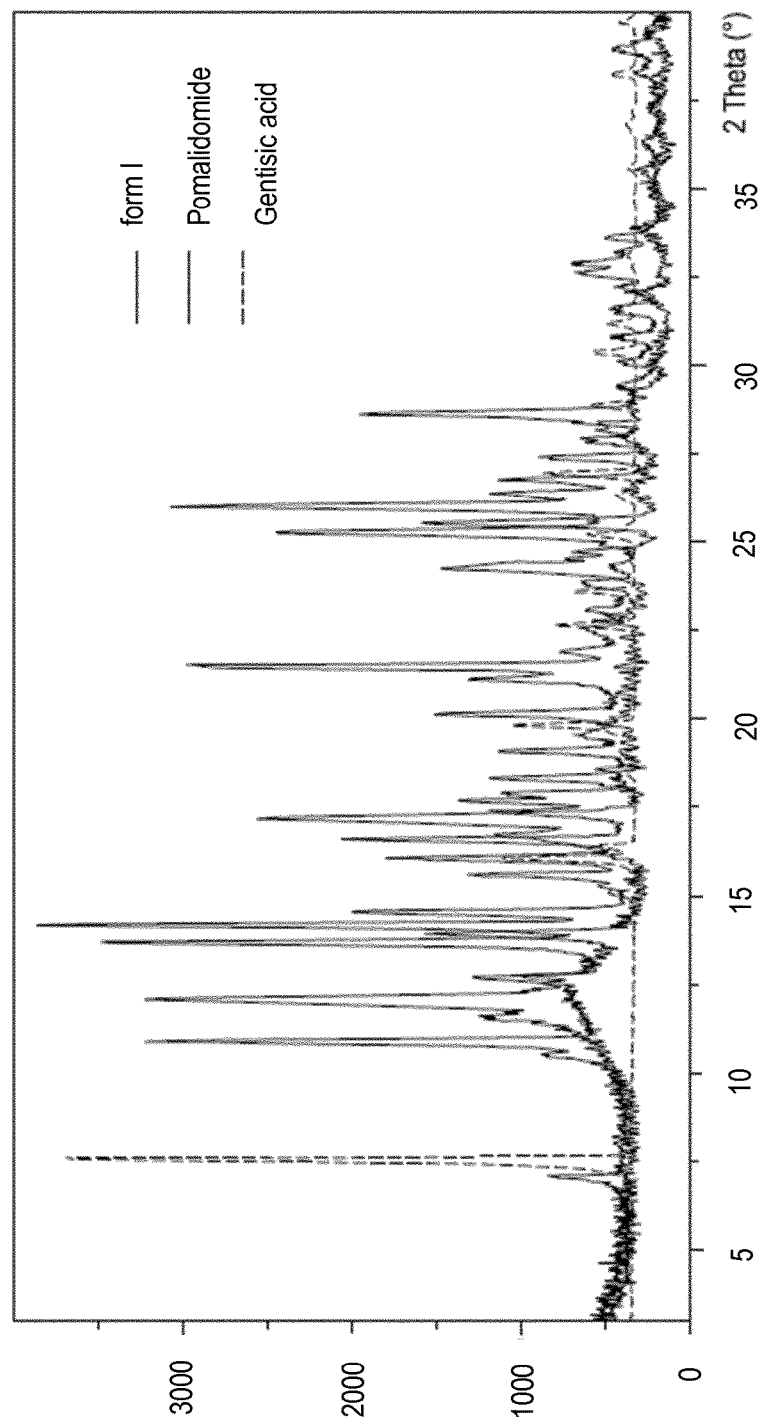
FIG. 7 is an XRPD diffractogram of comparison of the co-crystal of Pomalidomide and Gentisic acid Form 1 according to the invention compared to Pomalidomide Form O and Gentisic acid starting materials.

The XRPD spectrum of FIG. 7, pertaining to a mixture of Pomalidomide, Gentisic acid and their co-crystal, shows the presence of distinctive characteristic signals for both the starting materials Pomalidomide and Gentisic acid, such as for example the peaks 2θ around 7.5° and around 10.1° respectively, signals which are no longer detectable in the XRPD spectrum of the co-crystal of FIG. 8.

The Form 1 of the co-crystal Pomalidomide: Gentisic acid is at least characterized by peaks 2θ(°) at about 13.7, 14.2 and 26.0 as measured by XRPD.

By the term "peaks 2θ(°) at about", the indication is intended that the 2θ(°) value of the peaks in the XRPD diffractogram may vary not more than ±10%, preferably not more than ±5%, even more preferably not more than ±1% or ±0.5%.

The Form 1 of the co-crystal of Pomalidomide and Gentisic acid according to the present invention, characterized by XRPD analysis, shows at least the following signals with the respective relative intensities:

TABLE 2

| Pos. [°2θ] | d-spacing [Å] | Rel. Int. [%] |
|---|---|---|
| 13.7 | 6.4 | 89 |
| 14.2 | 6.2 | 100 |
| 26.0 | 3.4 | 81 |

The Form 1 of the co-crystal Pomalidomide:Gentisic acid is preferably characterized by at least peaks 2θ(°) at about 10.9, 13.7, 14.2, 21.5, 25.3 and 26.0 as measured by XRPD.

The Form 1 of the co-crystal of Pomalidomide and Gentisic acid according to the present invention, characterized by XRPD analysis, preferably has at least the signals shown in the following Table 3, with the respective relative intensities:

TABLE 3

| Pos. [°2θ] | d-spacing [Å] | Rel. Int. [%] |
|---|---|---|
| 10.9 | 8.1 | 73 |
| 13.7 | 6.4 | 89 |
| 14.2 | 6.2 | 100 |
| 21.5 | 4.1 | 77 |
| 25.3 | 3.5 | 64 |
| 26.0 | 3.4 | 81 |

The Form 1 of the co-crystal of Pomalidomide and Gentisic acid according to the present invention, characterized by XRPD analysis, has even more preferably at least the signals shown in the following table 4a with the respective relative intensities:

TABELLA 4a

| Pos. [°2θ] | d-spacing [Å] | Rel. Int. [%] |
|---|---|---|
| 10.9 | 8.1 | 73 |
| 13.7 | 6.4 | 89 |
| 14.2 | 6.2 | 100 |
| 14.6 | 6.1 | 47 |
| 16.0 | 5.5 | 43 |
| 16.6 | 5.3 | 51 |
| 17.7 | 5.0 | 30 |
| 20.2 | 4.4 | 34 |
| 21.5 | 4.1 | 77 |
| 25.2 | 3.5 | 50 |
| 25.3 | 3.5 | 64 |
| 26.0 | 3.4 | 81 |
| 28.6 | 3.1 | 48 |

Preferably, the Form 1 of the co-crystal of Pomalidomide and Gentisic acid according to the present invention, characterized by XRPD analysis, has at least the signals shown in the following Table 4b with the respective relative intensities:

TABELLA 4b

| Pos. [°2θ] | d-spacing [Å] | Rel. Int. [%] |
|---|---|---|
| 10.92 | 8.10 | 73 |
| 13.72 | 6.45 | 89 |
| 14.19 | 6.24 | 100 |
| 21.50 | 4.13 | 77 |
| 25.30 | 3.52 | 64 |
| 26.02 | 3.42 | 81 | more preferably at least the signals shown in the following table 4c with the respective relative intensities TABELLA 4c

| Pos. [°2θ] | d-spacing [Å] | Rel. Int. [%] |
|---|---|---|
| 10.92 | 8.10 | 73 |
| 13.72 | 6.45 | 89 |
| 14.19 | 6.24 | 100 |
| 14.57 | 6.08 | 47 |
| 16.06 | 5.52 | 43 |
| 16.61 | 5.34 | 51 |
| 17.68 | 5.02 | 30 |
| 20.18 | 4.40 | 34 |
| 21.50 | 4.13 | 77 |
| 25.22 | 3.53 | 50 |
| 25.30 | 3.52 | 64 |
| 26.02 | 3.42 | 81 |
| 28.64 | 3.12 | 48 |

Figure 3:
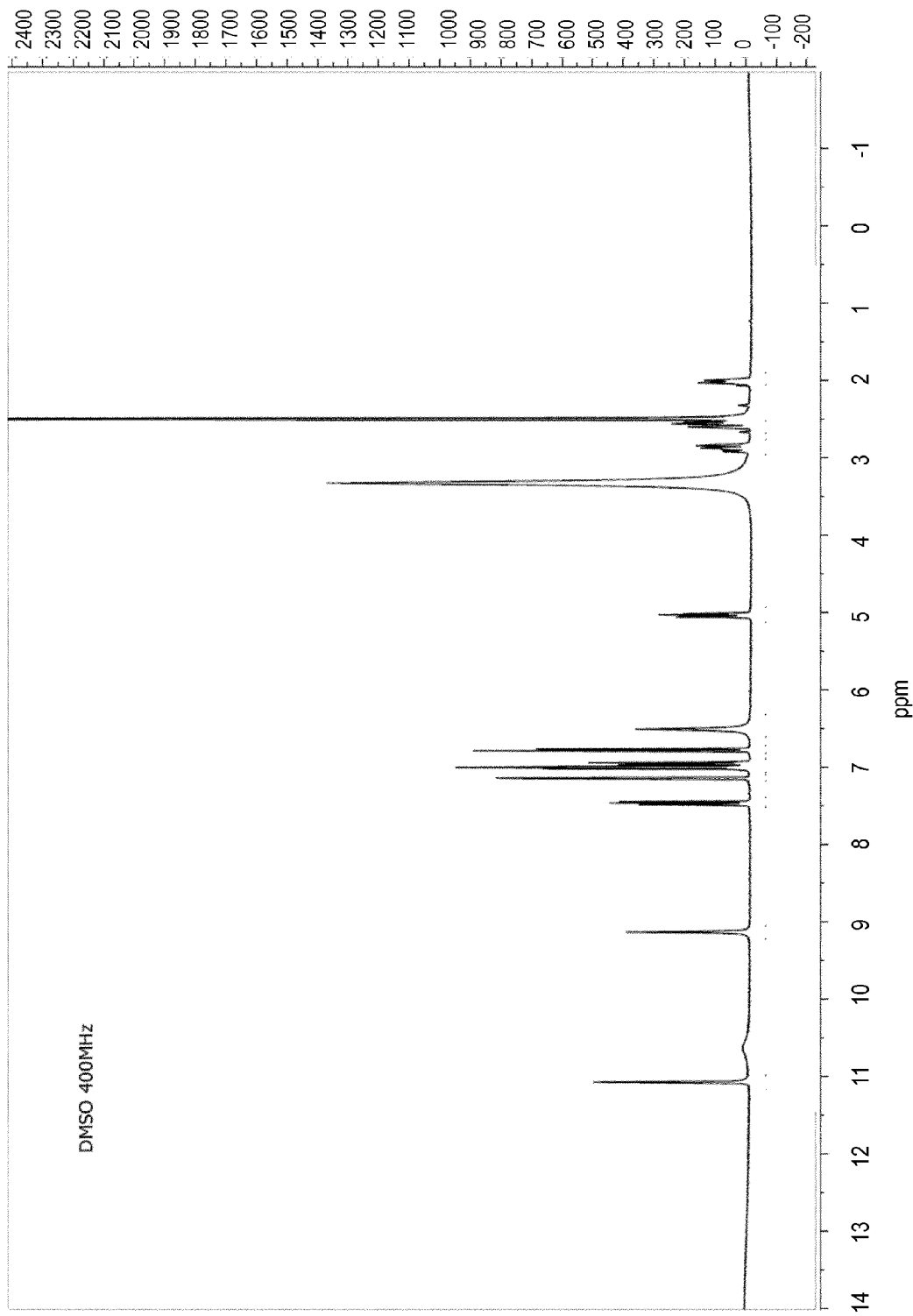
FIG. 3 is a $^1$H-NMR spectrum of the co-crystal of Pomalidomide and Gentisic acid according to the invention.
Figure 5:
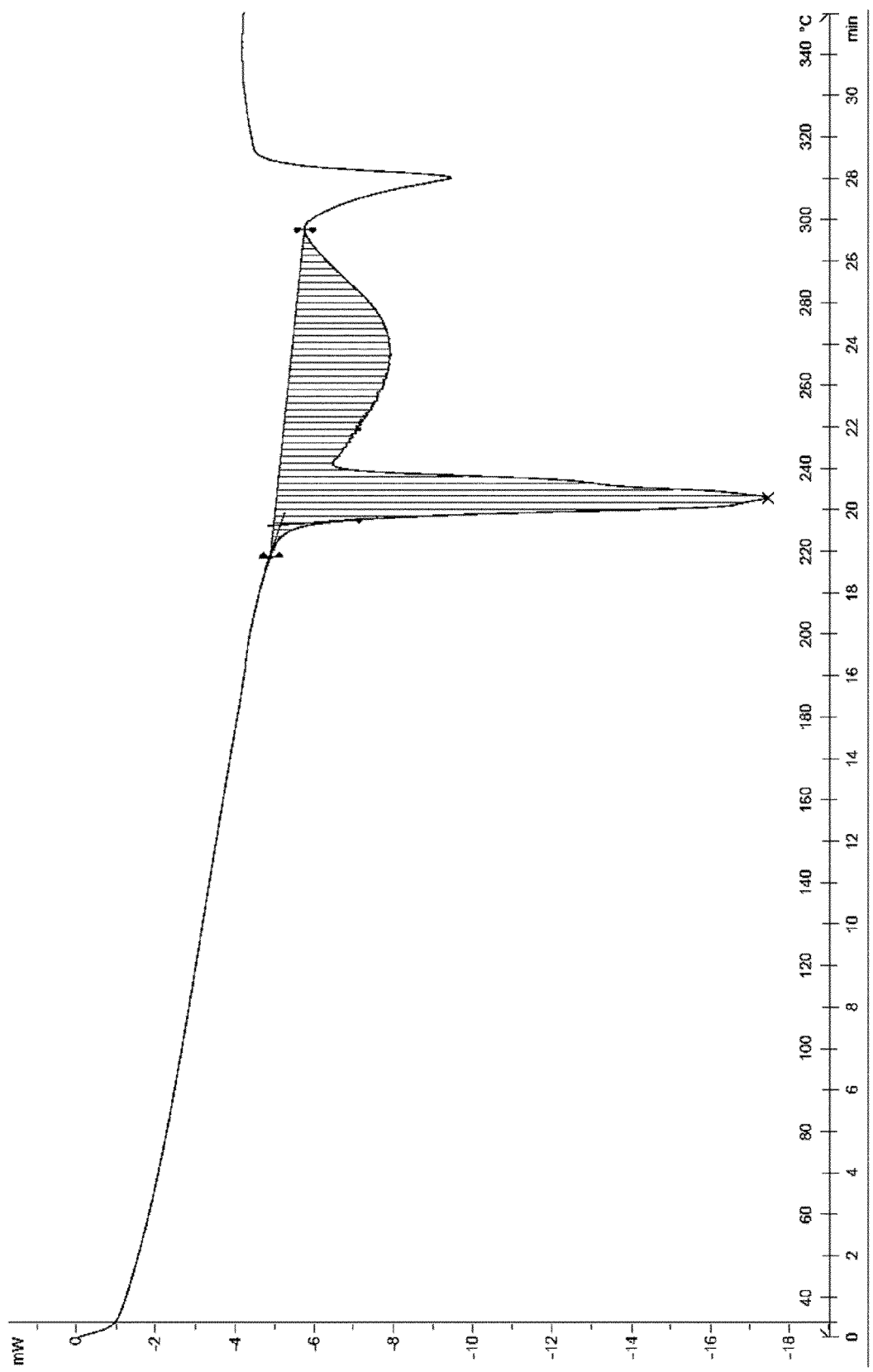
FIG. 5 is a DSC diagram of the co-crystal of Pomalidomide and Gentisic acid Form 1 according to the invention.
Figure 6:
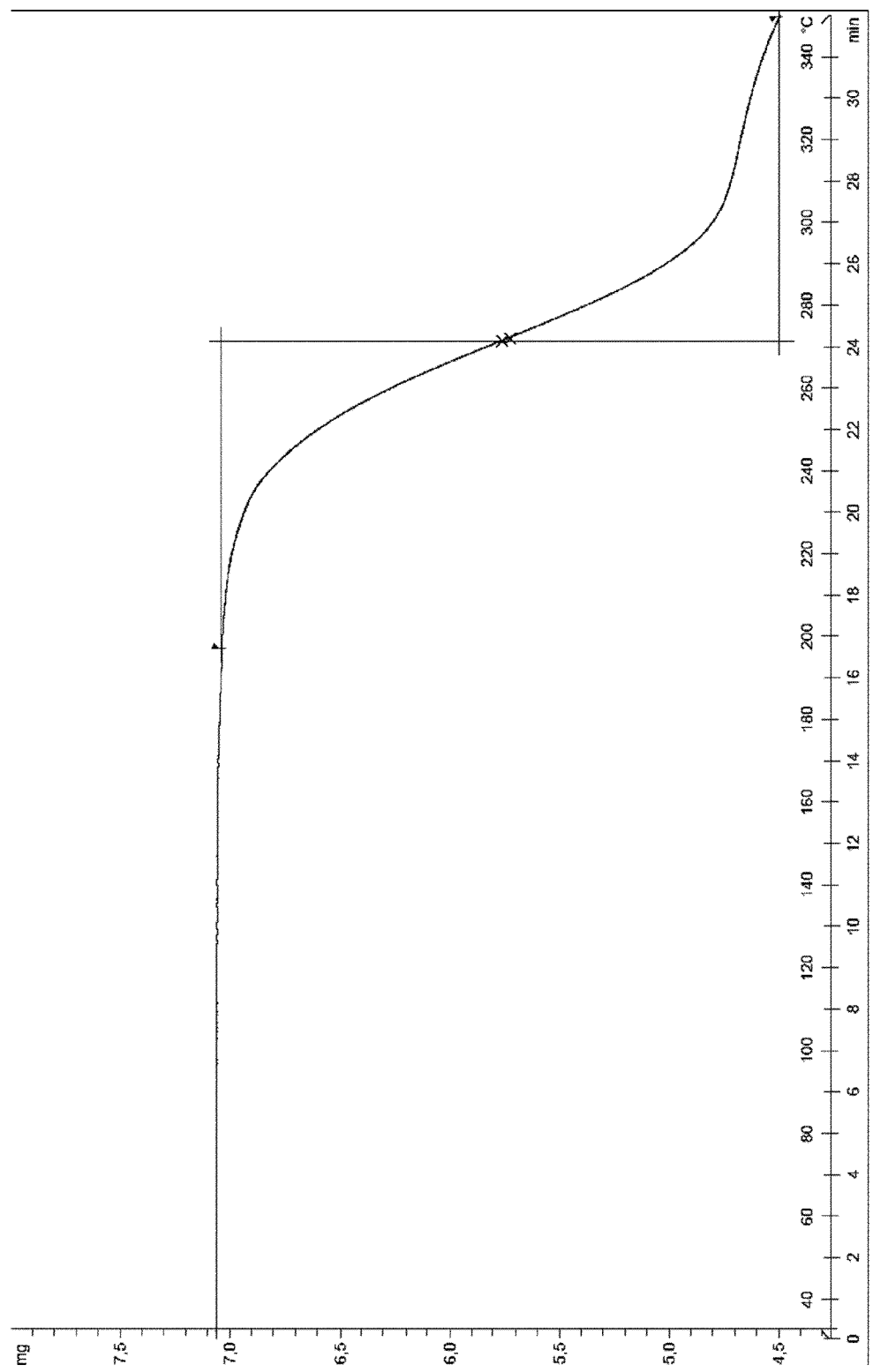
FIG. 6 is a TGA diagram of the co-crystal of Pomalidomide and Gentisic acid Form 1 according to the invention.

The present co-crystal of Pomalidomide and Gentisic acid has been further characterized by means of $^1$H-NMR analysis, DSC, and TGA (FIGS. 3, 5 and 6 respectively).

Figure 9:
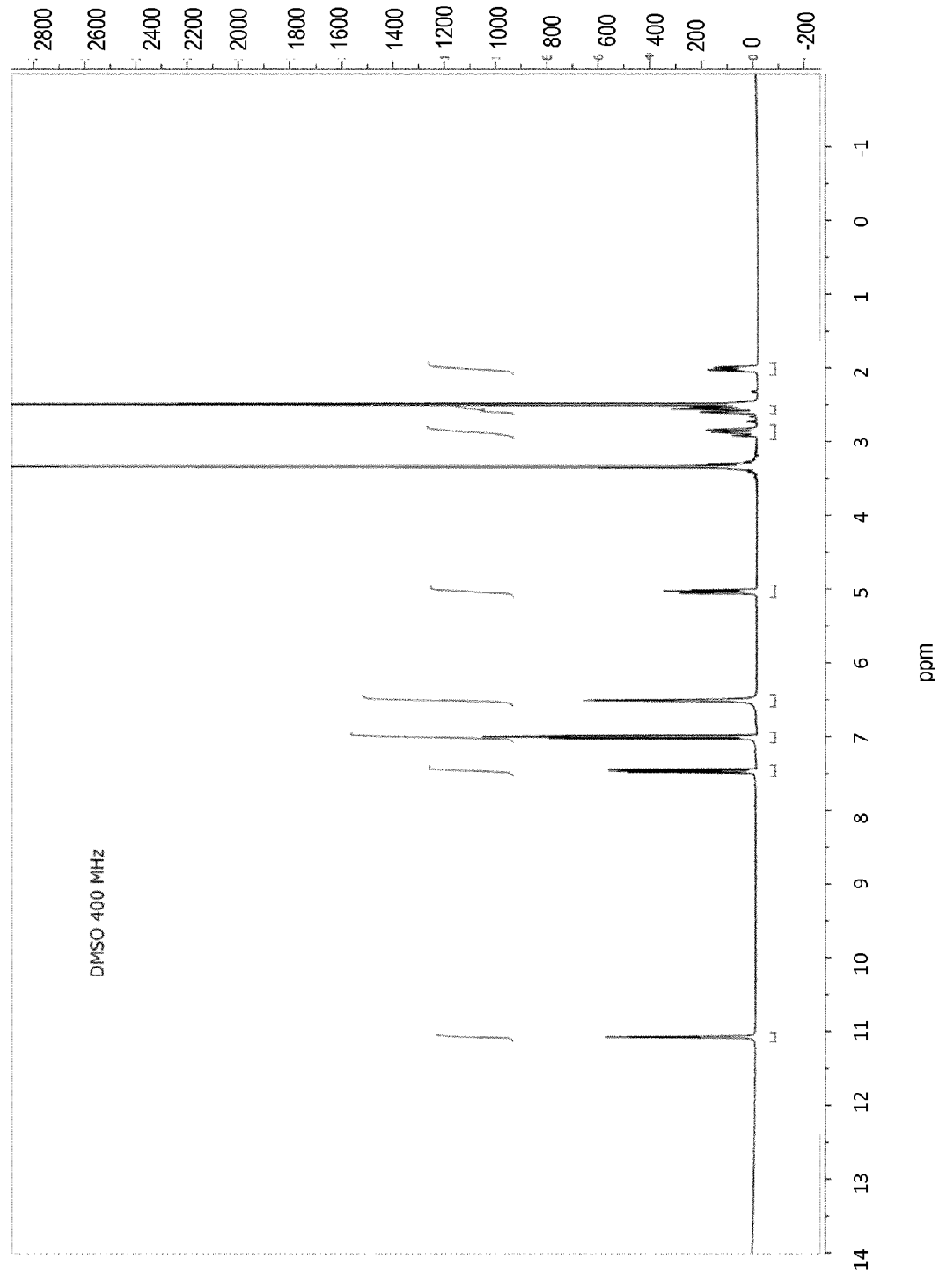
FIG. 9 is a $^1$H-NMR spectrum of Pomalidomide Form O.
Figure 10:
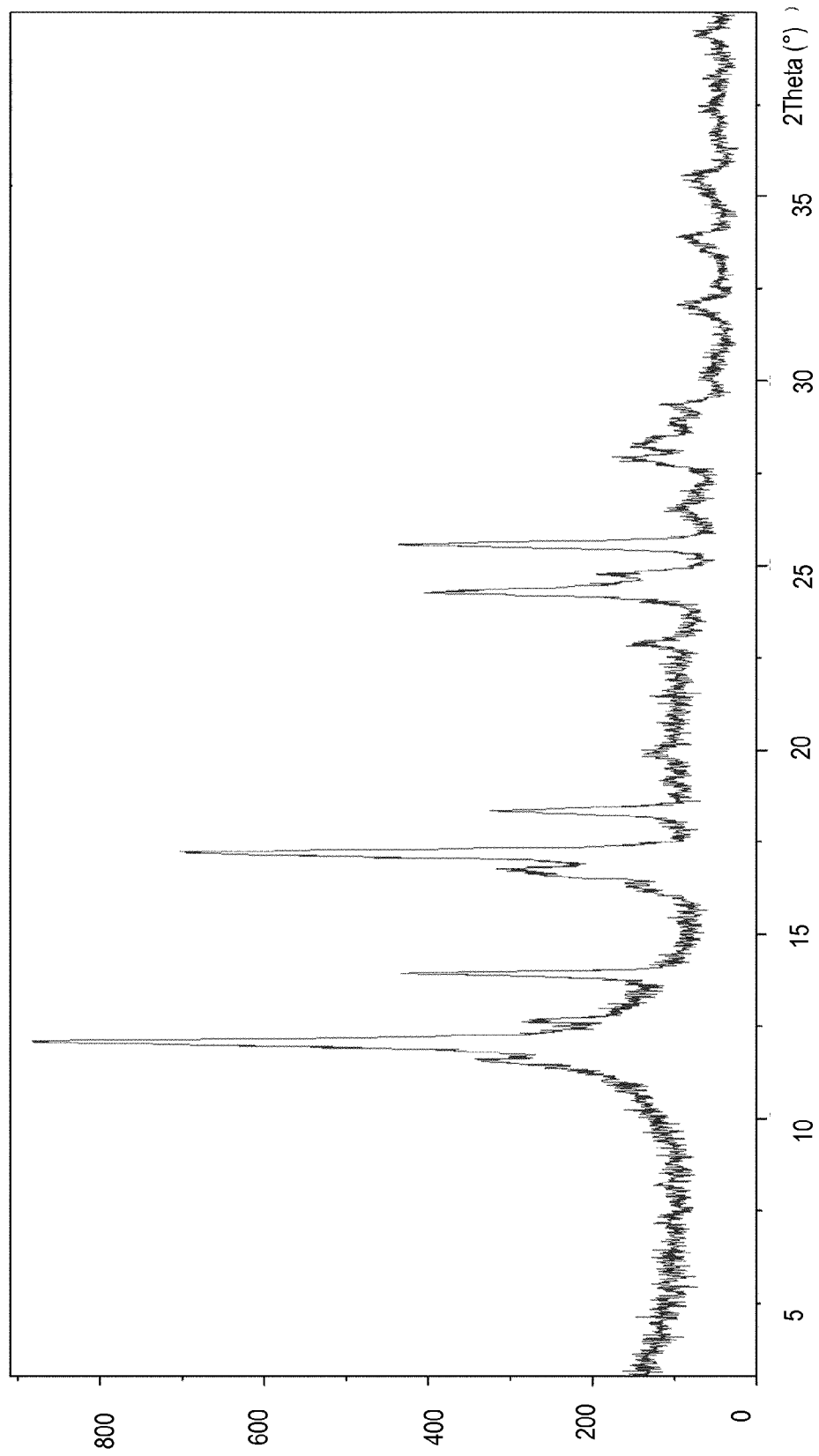
FIG. 10 is an XRPD diffractogram of Pomalidomide Form O.
Figure 11:
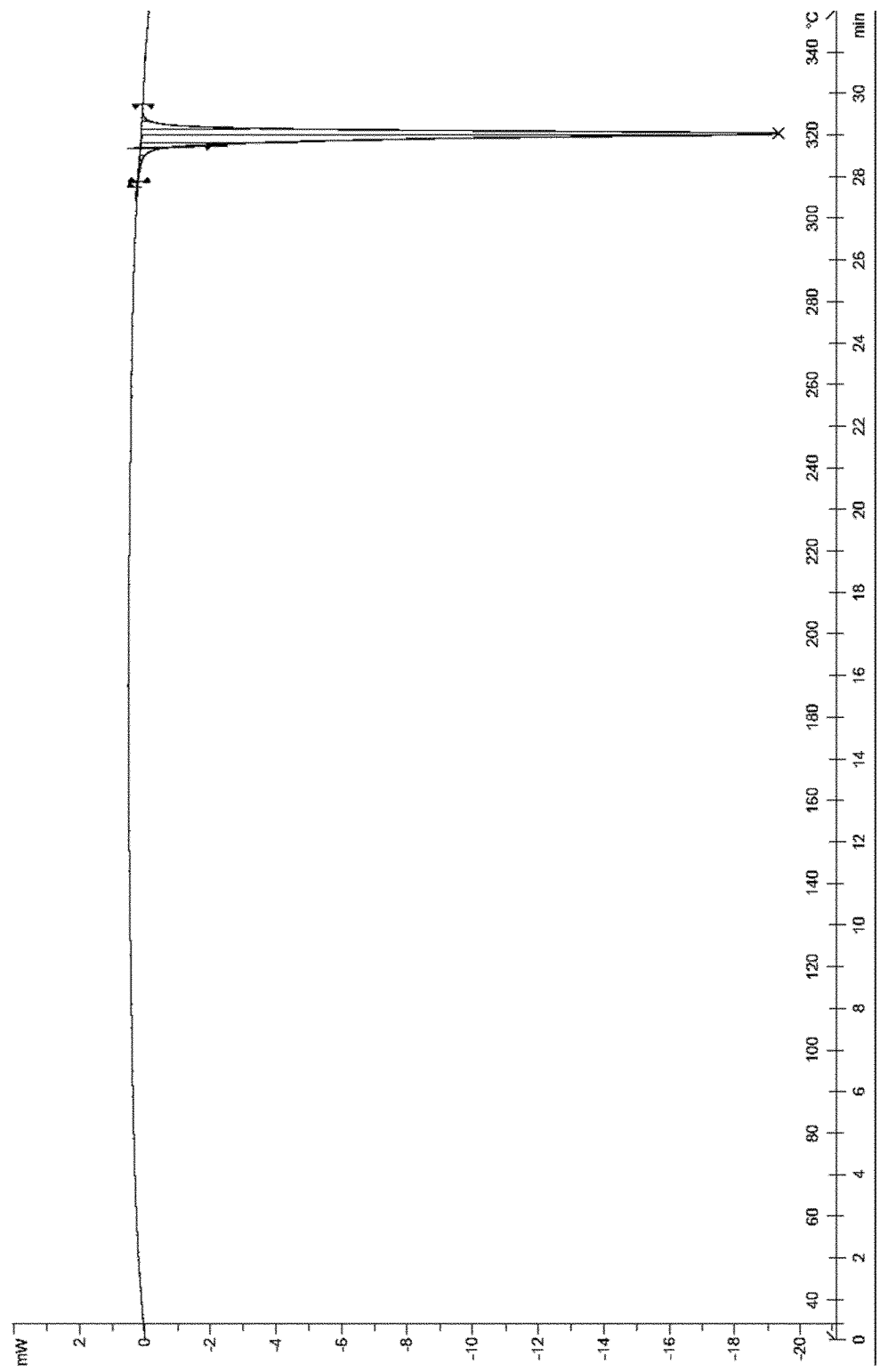
FIG. 11 is a DSC plot of Pomalidomide Form O.
Figure 12:
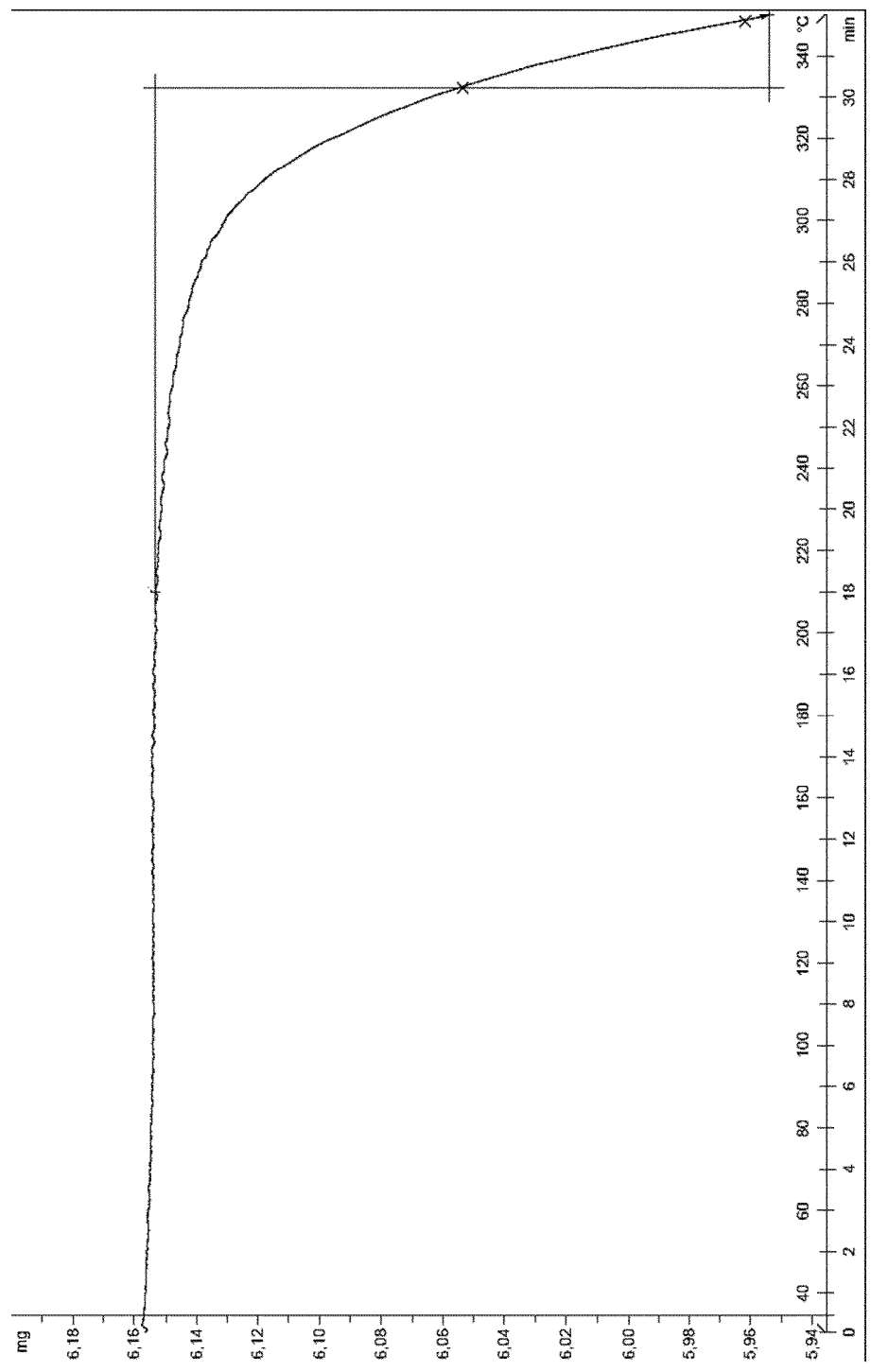
FIG. 12 is a TGA plot of Pomalidomide Form O.

The $^1$H-NMR analysis of FIG. 3 confirms in the co-crystal the presence of Pomalidomide and Gentisic acid in a molar ratio 1:1 (see in comparison the NMR trace of the single Pomalidomide, of FIG. 9). From thermal analyses of FIGS. 5 and 6 it is noticed that the present co-crystal melts at about 232° C. (start of the peak at about 226° C.), that it degrades at higher temperatures and that it would not be a hydrated form since it does not release water with weight loss prior to melting.

By the term about 232° C. it is meant a temperature range of ±10%, preferably of ±5%, more preferably of ±1% or ±0.5% with respect to the temperature 232° C. of the melting peak. The present co-crystal is characterized by the DSC diagram shown in FIG. 5.

The co-crystal of Pomalidomide: Gentisic acid (1:1) according to the invention has a higher solubility in water than Pomalidomide, especially at acidic pH, as demonstrated in Example 9 of the present experimental part.

The present co-crystal is stable in aqueous medium and does not tend to form hydrates, as it is apparent from the tests of preparation in water of Example 8 and from the tests of stability under high relative humidity conditions as described in Example 10. Advantageously, the present co-crystal is stable under normal storage conditions and pharmaceutical processing (for example wet granulation, compression, compaction etc. . . . ).

The present co-crystal, thanks to the higher water solubility is particularly interesting from a pharmaceutical point of view, as it would favor the administration of Pomalidomide in a more absorbable form, especially at gastric level, even at high doses.

Another advantage in the use of the present co-crystal of Pomalidomide with respect to Pomalidomide, lies in its higher molecular weight. The current therapeutic dose of Pomalidomide varies from 1 to 4 mg per capsule. Understandably, it is rather difficult to mix homogeneously such low quantities of active principle with the excipients ensuring the dispersion.

Due to the increased molecular weight, the present co-crystal is used in bigger quantities per dosage unit, thus allowing a better distribution of the active substance in the excipients of the solid forms.

The present co-crystal is also useful as an intermediate for purifying Pomalidomide.

In fact the Applicant has observed that, starting from crude Pomalidomide, it is possible to obtain the present co-crystal with a high degree of purity.

The present co-crystal can be used directly as the solid form of administration of the Pomalidomide in suitable formulations, or serve as an intermediate for the subsequent release of Pomalidomide having a higher level of purity.

The present co-crystal can be directly administered because the co-former, Gentisic acid, is accepted by the pharmacopoeias.

If instead the co-crystal is used as an intermediate for purification, purified Pomalidomide can be recovered from the co-crystal through suitable treatments, such as for example by shaking the co-crystal in suitable solvents such as ethyl acetate, methyl-isobutylketone, ethanol, isopropanol and acetone, for sufficient time as described in the present experimental part.

A second aspect of the present invention is a process for the preparation of the co-crystal Pomalidomide: Gentisic acid according to the present invention.

This process, comprises
 a) providing Pomalidomide in a predetermined amount;
 b) providing Gentisic acid in a molar ratio of not more than 4:1, 3:1, 2:1, 1.5:1 or 1.2:1 with respect to Pomalidomide;
 c) contacting Pomalidomide and Gentisic acid and optionally at least one co-crystal of Pomalidomide and Gentisic acid:
  c1) in solution or in suspension, in a suitable solvent, or
  c2) by means of grinding, optionally in the presence of traces of an appropriate solvent,
 d) maintaining in contact Pomalidomide and Gentisic acid for the time necessary to form the co-crystal in accordance with the first aspect of the present invention, and optionally
 e) separating the co-crystal from the solvent.

The present process is characterized by one or more of the following features, taken alone or in combination.

The present process is based on the use of Pomalidomide and Gentisic acid as starting materials. Pomalidomide (PM 273.24) can be prepared according to one of the known processes, for example according to the general processes of preparation of the class of 4-amino-2-(2,6-dioxopiperidin-3-yl)-isoindol described in U.S. Pat. No. 6,395,754 and U.S. Pat. No. 5,635,517 or, in particular, in the racemic form as described in the patent application WO2007005972 filed by Celgene Corporation, or as a single enantiomer, in accordance with U.S. Pat. No. 6,476,052.

Preferably Pomalidomide of the present process is in the racemic form.

In the preparation of the present co-crystal, Pomalidomide starting material can be in amorphous form or in any crystal form, for example in Form O, Form A, Form 1, Form B or Form M, preferably in Form O.

In the present process Pomalidomide starting material can be crude Pomalidomide, still in the reaction medium or, preferably, isolated from it and, optionally, containing one or more impurities or traces of solvent. Advantageously, the present preparation process of the co-crystal of Pomalidomide and Gentisic acid allows the reduction of the impurities contained in the crude, thus obtaining a co-crystal of high purity, in particular after at least one further crystallization.

Alternatively, Pomalidomide starting material can be Pomalidomide partially or completely purified. Gentisic acid used in the preparation of the co-crystal can be utilized in a molar ratio comprised between 4:1 and 1:4, preferably between 3:1 to 1:3, between 2:1 and 1:2, more preferably between 1:1, 5 and 1.5:1, even more preferably between 1:1.2 and 1.2:1 or about 1:1, with reference to Pomalidomide.

Preferably in the preparation of the co-crystal, Gentisic acid is used in molar excess with respect to Pomalidomide.

Preferably in the preparation of the co-crystal, Gentisic acid is used in molar excess with respect to Pomalidomide not more than 4:1, 3:1, 2:1, 1.5:1 or 1.2:1.

In the present process the step of contacting Pomalidomide and Gentisic acid can be realized in different ways.

In a first embodiment of the present process, Gentisic acid may be added directly to the final reaction medium which contains crude Pomalidomide, partially dissolved or suspended, preferably seeding with the co-crystal Form 1.

Appropriately selecting the solvent, the concentrations and the operating temperatures, it is possible to obtain and directly precipitate the co-crystal, with a purity higher than the crude Pomalidomide, advantageously simplifying the process and reducing times and costs. In fact it is possible to obtain the desired product with a higher degree of purity in a single step.

In an alternative embodiment, it is possible to dissolve isolated, crude or already purified Pomalidomide, in a suitable solvent, and to precipitate the co-crystal by addition of Gentisic acid (precipitation from solution or crystallization) preferably after seeding with the co-crystal.

In another embodiment, preferred, of the present process, Pomalidomide and Gentisic acid are suspended in a solvent, under stirring (slurrying), preferably seeding with the co-crystal Form 1. Preferably Gentisic acid (MW 154.12) is used in a molar ratio comprised between 4:1 and 1:4, preferably between 1:3 and 3:1, between 2:1 and 1:2, more preferably between 1:1.5 and 1.5:1, even more preferably between 1:1.2 and 1.2:1.

Preferably, Gentisic acid is used in molar excess with reference to Pomalidomide.

Preferably in the preparation of the co-crystal, Gentisic acid is used in molar excess with respect to Pomalidomide not more than 4:1, 3:1, 2:1, 1.5:1 or 1.2:1.

Preferably Gentisic acid is used in a molar ratio of between 2.1:1 and 1.1:1 compared to Pomalidomide.

Preferably, the solvent used for the suspension is selected from acetonitrile, water, isobutyl acetate and mixtures thereof, more preferably acetonitrile, water or mixtures thereof.

Preferably the solvent is used in a volumetric ratio (ml/g) (volume of solvent relative to the weight of the Pomalidomide) between 1 and 15, more preferably between 5 and 12, even more preferably between 6 and 10 ml/g.

Preferably the solvent is used in a volumetric ratio (ml/g) (volume of solvent relative to the weight of the Pomalidomide) of less than 15, more preferably less than 10, even more preferably less than 8 ml/g.

Preferably the temperature of the solution or suspension is comprised between room temperature and 60° C., more preferably about 50° C.

Preferably the solution or suspension is stirred for a period of between 30 minutes and 24 hours, more preferably between 1 and 12 hours, even more preferably between 1.5 and 5 hours.

Preferably, the formation of the co-crystal it favored by adding to the suspension at least one co-crystal of Pomalidomide: Gentisic acid Form 1.

In a preferred embodiment of the present process, Pomalidomide and Gentisic acid are suspended in a molar ratio of 1:2, in 6.6 volumes of acetonitrile (ml/g), under stirring (slurrying) for one night, at room temperature, seeding with co-crystal Form 1.

In a preferred embodiment of the present process, Pomalidomide and Gentisic acid are suspended in a molar ratio of 1:2, in 10 volumes of water (ml/g), under stirring (slurrying) for one night, at 50° C., seeding with the co-crystal Form 1.

In a preferred embodiment of the present process, Pomalidomide and Gentisic acid are suspended in a molar ratio of 1:1.5 in 10 volumes of water (ml/g), under stirring (slurrying) for 3 hours, at 50° C., seeding with co-crystal Form 1.

Preferably the obtained co-crystal of Pomalidomide and Gentisic acid Form 1 is separated off from the solvent by centrifugation, decantation or filtration, preferably by filtration.

Alternatively, in the previous embodiments of the present process it is possible to proceed by reversing the order of addition, that is adding Pomalidomide or its solution or suspension into Gentisic acid dissolved or suspended in the appropriate solvent.

In another embodiment of the present process, Pomalidomide and Gentisic acid are ground together in the solid state, (co-grinding), optionally in the presence of traces of solvent (kneading) and optionally seeding with the co-crystal Form 1.

Preferably in the present process of co-grinding, Gentisic acid is used in a molar ratio comprised between 2:1 and 1:2, more preferably between 1.5:1 and 1:1.5, even more preferably between 1:1.2 and 1.2:1 or about 1:1 compared to Pomalidomide.

In case it is present, the solvent is preferably selected from water, chloroform, dimethylformamide, tetrahydrofuran, methanol, isopropyl alcohol and mixtures thereof, more preferably water.

Preferably in the co-grinding the solvent is used in trace amounts, preferably in a volumetric ratio solvent/weight of Pomalidomide (ml/g) less than 10 ml/g, than 5 ml/g, than 2 ml/g, than 1 ml/or than 0.5 ml/g.

The co-grinding can be performed for small quantities manually in the mortar or industrially, for example with mills (ball mills, vibrating mills or other) commonly used for the crushing of solids in the pharmaceutical field.

Preferably, the co-grinding is carried out at room temperature, optionally by cooling to prevent overheating.

Preferably, the optional solvent is separated from the co-crystal by evaporation, optionally under vacuum.

More preferably the step of contacting Pomalidomide and Gentisic acid is effected by suspension in a suitable solvent, under stirring (slurrying).

The preparation process of the present co-crystal, generally presents yields higher than 70%, than 80%, preferably 90% or more with reference to Pomalidomide starting material.

Optionally, the co-crystal obtained by the present process may be further purified, by crystallization preferably from acetonitrile, water or mixtures thereof.

A third aspect of the present invention is a pharmaceutical composition comprising a therapeutically effective amount of a solid crystal form of Pomalidomide chosen between Form B, Form M, a co-crystal of Pomalidomide and Gentisic acid and their mixtures, in accordance with the first aspect of the present invention and at least one pharmaceutically acceptable excipient.

Preferably, the present pharmaceutical composition is a solid form, for example a powder, a tablet, a capsule or a granule.

The therapeutically effective amount will depend on a number of factors such as, for example, the disease to be treated or prevented, its severity, the specific pharmaceutical composition used, the age, the body weight, the general state of health, the sex, and the patient's diet; the manner, the timing and the route of administration, the personal excretion rate of Pomalidomide, the duration of treatment, the co-administration of other drugs and other factors well known in the field.

Preferably, the present pharmaceutical composition comprises one or more of the solid forms of Pomalidomide of the present invention in a dosage of 0.1 to 100 mg, of 0.5 to 50 mg, of 0.5 to 25 mg, more preferably of 0.5 to 10 mg or of 0.5 to 5 mg per single dose.

Preferably, the present pharmaceutical composition comprises the co-crystal of Pomalidomide:Gentisic acid of the present invention in a dosage of 0.1 to 100 mg, of 0.5 to 50 mg, of 0.5 to 25 mg, more preferably of 0.5 to 10 mg or of 1 to 7 mg per single dose.

Preferably, the present pharmaceutical composition comprises the co-crystal of Pomalidomide:Gentisic acid according to the invention.

Preferably, the present pharmaceutical composition comprises the co-crystal of Pomalidomide:Gentisic acid according to the invention in an amount therapeutically equivalent to that currently contained in the individual commercial dosage forms comprising Pomalidomide (Imnovid capsules, from 1 to 4 mg of Pomalidomide per dosage unit).

Advantageously, the present pharmaceutical compositions may comprise proportionally smaller quantities of Pomalidomide, by virtue of the improved dissolution properties and, consequently, of the co-crystal absorption.

The at least one excipient of the present pharmaceutical composition, may be selected from those commonly used in the pharmaceutical field, in particular for solid dosage forms, such as those listed in "Remington: The Science and Practice of Pharmacy" 22nd Ed.

The present co-crystal of Pomalidomide and Gentisic acid, due to the considerable weight gain (PM Pomalidomide 273.24, PM co-crystal 427.36) with the same content of active ingredient, advantageously allows an improved dosing and a better dispersion in the solid ingredients.

Optionally, the present pharmaceutical composition may comprise at least a second active substance, preferably a steroid, an antibiotic or an anti-tumor, more preferably a steroid such as dexamethasone.

Examples of possible second active ingredients, suitable for the association in the present composition, are described in section 00128 of the patent application WO2013126326A1.

The pharmaceutical composition of the invention can be prepared according to known methods, for example as described in "Remington: The Science and Practice of Pharmacy" $22^{nd}$ Ed.

A fourth aspect of the present invention is a solid crystal form of Pomalidomide chosen between Form B, Form M, a co-crystal of Pomalidomide and Gentisic acid and their mixtures, in accordance with the first aspect of the present invention, for use as a medication.

A fifth aspect of the present invention is a solid crystal form of Pomalidomide chosen between Form B, Form M, a co-crystal of Pomalidomide and Gentisic acid and their mixtures, in accordance with the first aspect of the present invention, for use in the prevention and treatment multiple myeloma, inflammatory diseases, of autoimmune diseases, of immune diseases, of myelodysplastic syndrome, myeloproliferative disorders, anemia, of scleroderma, amyloidosis or other diseases associated with unwanted angiogenesis.

In particular, the present solid forms of Pomalidomide and their pharmaceutical compositions are suitable for use in the prevention or treatment of pathologies such as those listed from paragraph 00124 to paragraph 00126 of the patent application WO2013126326A1.

A sixth aspect of the present invention is a process for the purification of Pomalidomide which comprises a) providing crude Pomalidomide in a predetermined amount;

b) providing Gentisic acid in a molar ratio of not more than 4:1, 3:1, 2:1, 1.5:1 or 1.2:1, with respect to Pomalidomide;

c1) contacting the crude Pomalidomide and Gentisic acid in solution or in suspension in a suitable solvent, optionally in the presence of at least one co-crystal of Pomalidomide:Gentisic acid;

d) maintaining in contact Pomalidomide and Gentisic acid for the time necessary to form the co-crystal in accordance with the first aspect of the present invention, e) separating the obtained co-crystal from the solvent, f) optionally crystallize the co-crystal from an appropriate solvent, and g) recovering purified Pomalidomide from the co-crystal, preferably by suspension in an appropriate solvent.

The term crude Pomalidomide means a Pomalidomide containing at least an impurity such as a residue of one or more starting materials of the synthesis or reaction by-products, contained in total amount generally less than 10%, less than 5%, preferably lower to 3%.

The present purification process is characterized by one or more of the features already listed above for the preparation process of the present co-crystal, taken alone or in combination.

In particular, Pomalidomide starting material in the present process is a crude Pomalidomide, still in the reaction medium, or isolated from it and containing one or more impurities, named crude Pomalidomide being for example prepared according to the known processes previously mentioned.

In one embodiment, Gentisic acid may be added directly to the final reaction medium that contains crude Pomalidomide dissolved or suspended, preferably seeding with the co-crystal Form 1. In a preferred embodiment, the present purification process is performed by suspension of the crude Pomalidomide in a suitable solvent selected from acetonitrile, water, isobutyl acetate and mixtures thereof, more preferably between acetonitrile, water or mixtures thereof and subsequent addition of Gentisic acid under stirring, preferably seeding with the co-crystal Form 1.

Preferably, Gentisic acid (MW 154.12) is used in a molar ratio comprised between 4:1 and 1:4, between 1:3 and 3:1, preferably between 2:1 and 1:2, more preferably between 1:1.5 and 1.5:1 or between 1:1.2 and 1.2:1.

Preferably, Gentisic acid is used in molar excess with respect to Pomalidomide.

Preferably Gentisic acid is used in a molar ratio comprised between 2.1:1 and 1.1:1 with respect to Pomalidomide.

Preferably, in the present purification process of Pomalidomide, Gentisic acid is used in a molar excess with respect to Pomalidomide not more than 4:1, to 3:1, not more than 2:1, to 1.5:1 or to 1.2:1.

Preferably the solvent is used in a volumetric ratio (ml/g) (volume of solvent relative to the weight of the Pomalidomide) comprised between 1 and 15, more preferably between 5 and 12, even more preferably between 6 and 10 ml/g.

Preferably the solvent is used in a volumetric ratio (ml/g) (volume of solvent relative to the weight of the Pomalidomide) of less than 15, more preferably less than 10, even more preferably less than 8 ml/g.

Preferably the temperature of the solution or suspension comprising Pomalidomide and Gentisic acid is comprised between room temperature and 60° C., more preferably it is between 35° C. and 55° C., even more preferably around 50° C.

Preferably the solution or suspension is stirred for a period comprised between 30 minutes and 24 hours, more preferably between 1 and 12 hours, even more preferably between 1.5 and 5 hours.

Preferably the obtained co-crystal of Pomalidomide and Gentisic acid Form 1 is separated off from the solvent by centrifugation, decantation or filtration, preferably by filtration. Optionally, the co-crystal of Pomalidomide and Gentisic acid can be further purified by crystallization from suitable solvents, preferably from acetonitrile. Preferably, Pomalidomide is recovered from the present co-crystal through suitable treatments, such as for example the stirring of the co-crystal in suitable solvents such as ethyl acetate, methyl-isobutylketone, ethanol, isopropanol and acetone, for a sufficient time as reported in this experimental part.

In order to increase the degree of purity, it is possible to repeat the steps of formation and separation of the co-crystal and the step of recovery of Pomalidomide.

Advantageously the present purification process allows the recovery of a purified Pomalidomide, i.e. with an impurity content lower than the crude starting material, as exemplified in Example 10, with high yields, generally better than in the known methods (for example the process of crystallization from DMSO/water).

For illustration purposes and not limiting of the present invention, the following examples are now given.

EXAMPLES

Analytical Instrumentation and Analytical Operating Conditions

The XRPD data herein shown were measured using a PANalytical XPert diffractometer with a Cu-Kα radiation in Bragg-Brentano geometry. The system was equipped with a one-dimensional detector RTMS (Real Time Multiple Strip). The diffractograms were acquired from 3° to 40° (2θ) with a scan speed of 0.0821°/s. The samples were prepared by compressing a thin layer of the product on the surface of a quartz sample holder. For safety reasons, the sample was covered with a plastic film. The XRPD spectrum of this plastic material had an amorphous profile (FIG. 4, the background noise) and did not interfere with the signals of the crystal forms analyzed.

The DSC analysis was performed with a Mettler DSC822e instrument. The samples were prepared by weighing the compound in a 40 µL aluminum crucible with pierced lid, then heating under nitrogen (flow 50 mL/min) at 10° C./min from 30 to 350° C.

The thermogravimetric or TGA analysis was performed with a thermogravimetric analyzer Mettler TGA/SDTA851e. The samples were prepared by weighing the compound in a 70 µL aluminum crucible with pierced lid, then heating under nitrogen (flow 50 mL/min) at 10° C./min from 30 to 350° C.

The $^1$H-NMR proton magnetic resonance analyses were carried out in deuterated dimethylsulfoxide (DMSO-D6) in a Varian Mercury 400 spectrometer equipped with 5 mm broadband probe ATB 1H/19F/X. The spectra were acquired by dissolving 5-10 mg of sample in 0.6 ml of deuterated solvent.

The HPLC analysis (high-performance liquid chromatography), to determine the purity of the samples, was carried out in accordance with the following operating conditions and instrumentation:

Column: Zorbax Eclipse C18 (XDB), 150×4.6 mm, 5 micron

Sample concentration: 0.5 mg/ml in ACN:H2O:H3PO4 (65:35:0.2 v/v)

Mobile phase: A: ACN:H2O:H3PO4 (5:95:0.1 v/v), B: ACN

Gradient: 1 min (90:10), 20 minutes (75:25)

Temperature: 40° C.

Flow rate: 1 ml/min

UV detector (wavelength): 225 nm

Injection: 5 ml

Acquisition time: 21 min

Example 1

Preparation and Characterization of Pomalidomide Form O 15 g of racemic Pomalidomide Form O were prepared following the procedure described in patent application WO2007005972, in particular according to example 17. The final crystallization was accomplished by DMSO/water, as described in this patent application.

The product was characterized by $^1$H-NMR, XRPD, DSC, and TGA (FIGS. 9-12).

Preliminary Solubility Study

A preliminary study of the solubility of Pomalidomide Form O was performed in a range of solvents and under the operating conditions given in the following table 5:

TABLE 5

| $H_2O$ | DMSO | $MeNO_2$ | DMF | NMP | EtOH |
|---|---|---|---|---|---|
| <1 mg/mL RT | 6 vol. RT | >80 vol. RT; <80 vol. reflux | 26 vol. RT | 8 vol. RT | <1 mg/mL RT |
| Anisole | AcOiBu | Dioxane | $Et_2O$ | MIBK | $CHCl_3$ |
| >80 vol. RT; >80 vol. reflux | >80 vol RT; >80 vol. reflux | >80 vol. RT <80 vol. reflux | >80 vol. RT; >80 vol. reflux | >80 vol. RT; >80 vol. reflux | >80 vol. RT; >80 vol. reflux |

Abbreviations:
DMSO dimethyl sulfoxide;
DMF dimethylformamide;
NMP N-methyl pyrrolidone;
AcOiBu isobutyl acetate;
MIBK methyl-isobutylketone;
EtOH ethanol.

The obtained data confirm the literature values of poor solubility of Pomalidomide in many organic solvents and, in particular, in water.

Example 2

Preparation and Characterization Pomalidomide Form A 1.2 g of racemic Pomalidomide Form A were prepared following the procedure described in patent application WO2013126326A1 paragraph 00233, suspending Pomalidomide Form O of Example 1 in water and acetonitrile at 50° C. under stirring for 20 hours.

Figure 13:
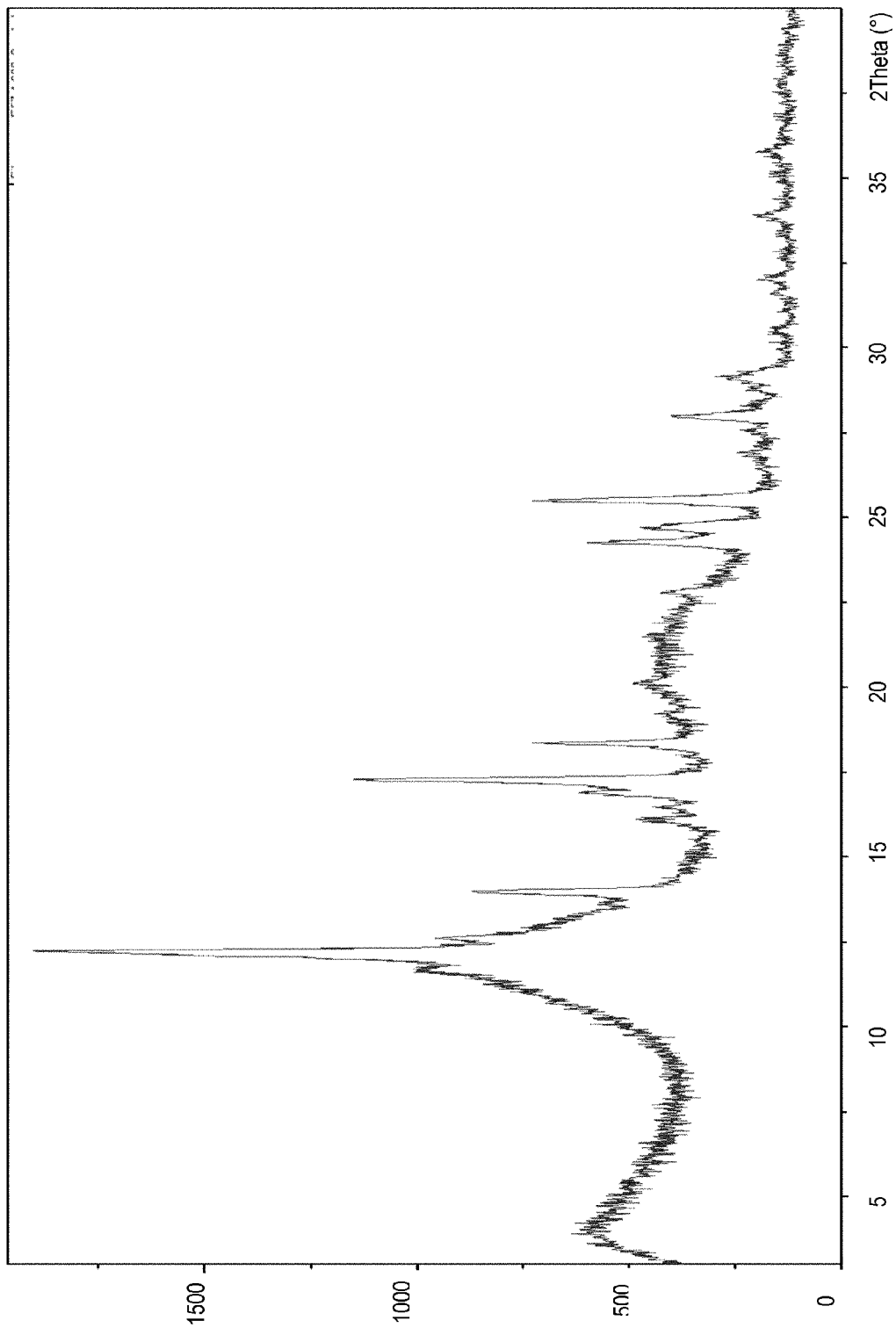
FIG. 13 is a XRPD diffractogram of Pomalidomide Form A.
Figure 14:
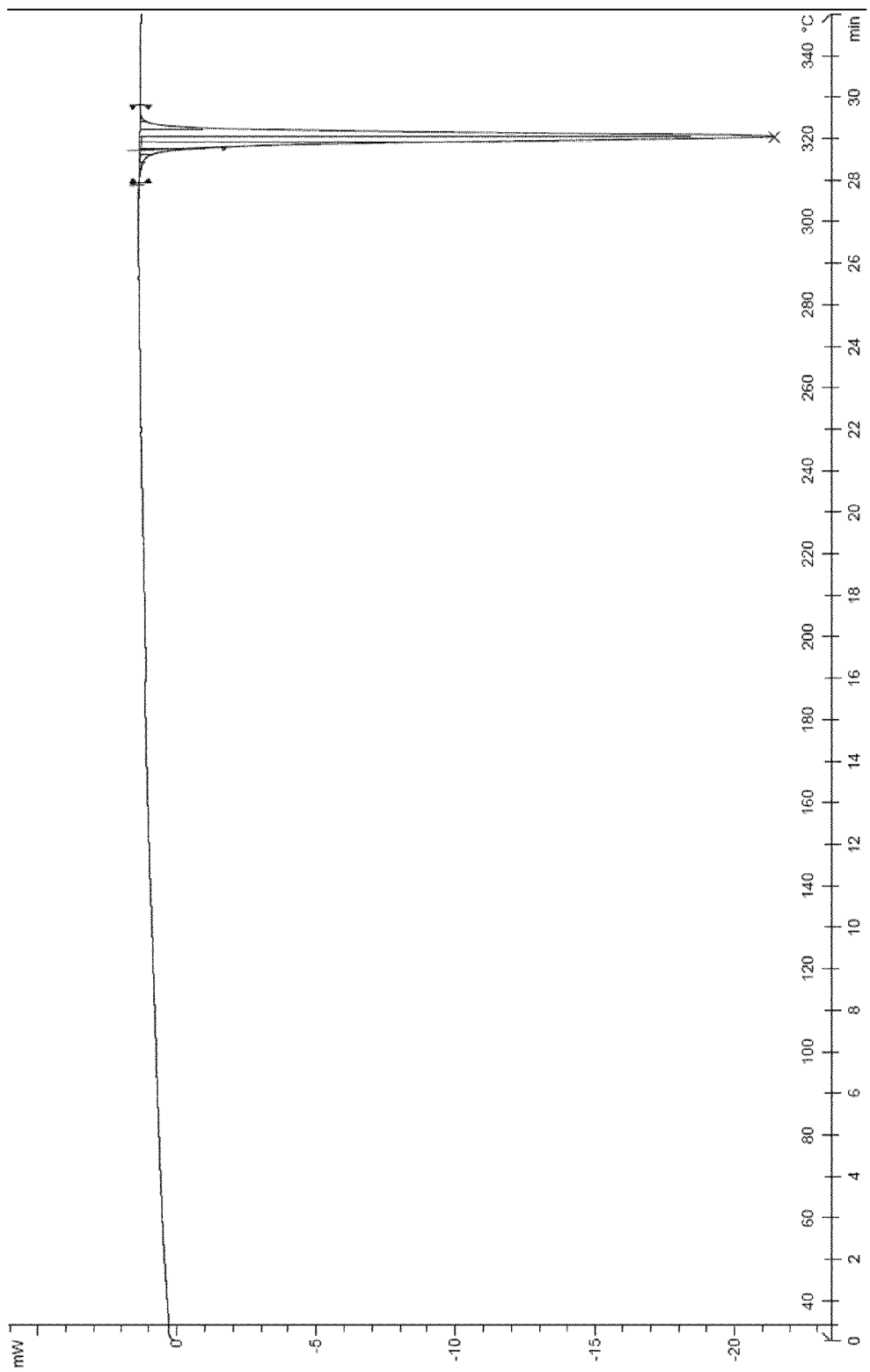
FIG. 14 is a DSC diagram of Pomalidomide Form A.

The product was characterized by XRPD and DSC (FIGS. 13 and 14).

Figure 4:
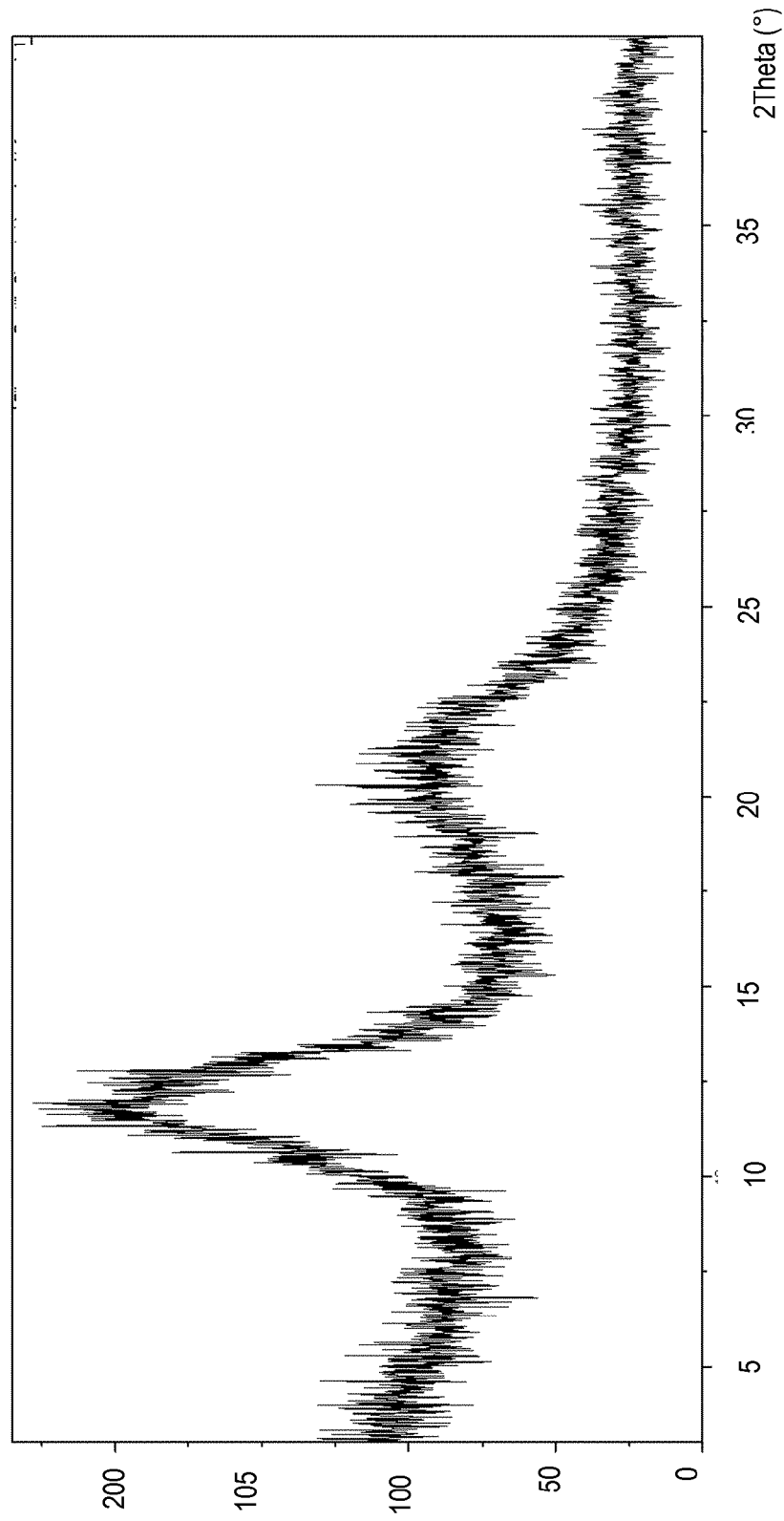
FIG. 4 is a diffractogram of the sample protection film, of substantially amorphous plastic material (background noise in the diffractograms).

The crystal Form A provides the same XRPD peaks of the product described in WO2013126326A1 (see FIG. 25) although in the present diffractogram (FIG. 13) the presence of the protective plastic film has added a profile of an amorphous, shown in FIG. 4, not detectable in FIG. 25 of said patent application.

Pomalidomide Form A is characterized by a sharp endothermic peak that starts at 317.14° C. (melting) (FIG. 14)

Example 3

Preparation and Characterization Pomalidomide Form B 1 g of Pomalidomide Form O prepared as in Example 1, wet with 10 ml of chloroform, were ground in a mortar for about 180 minutes and dried under vacuum, providing the new Pomalidomide Form B as a crystalline powder.

The new Pomalidomide Form B was characterized by XRPD (FIG. 1)

Alternatively, Pomalidomide Form B was obtained by grinding Pomalidomide Form O and L-tartaric acid (1:1), in the presence of chloroform, tetrahydrofuran or isopropanol.

The product thus obtained was used as a crystallization seed in other preparations of Pomalidomide Form B carried out by grinding Pomalidomide Form O in the presence of tetrahydrofuran or isopropanol respectively.

Example 4

Preparation and Characterization of Pomalidomide Form M 1 g of Pomalidomide Form O prepared as in Example 1, was suspended in 20 ml of isopropanol, seeded with crystals of Pomalidomide Form B and stirred overnight at room temperature, giving after filtration and drying, the new Pomalidomide Form M as crystalline powder.

The new Pomalidomide Form M was characterized by XRPD (FIG. 2)

Stability of Pomalidomide Form M (Exposure to Moisture)

Pomalidomide Form M was subjected to a moisture stability test. 100 mg of Pomalidomide Form M, prepared as described above, were maintained for one night at 100% relative humidity (RH 100%), at room temperature and analyzed by XRPD. Form M did not take-up any water in the structure and was not converted into another crystal form, showing a stability in compliance with the pharmaceutical use.

Example 5

Formation Screening of Pomalidomide Co-Crystals

Formation experiments of Pomalidomide co-crystal were performed starting from 50 mg of Pomalidomide Form O with different co-formers, by varying the molar ratios (R mol) of Pomalidomide vs. Co-former, the method and the type of solvent, as shown in the following Table 6:

TABLE 6

| Co-former | R mol (PMD/AG) | Method | Solvents | Result |
| --- | --- | --- | --- | --- |
| Urea | 1:1 | Wet milling | $H_2O$, $CHCl_3$, DMF, THF, MeOH, IPA | No |
| Urea | 1:2 | Suspension | MeOH | No |
| Oxalic acid | 1:1 | Wet milling | $H_2O$, $CHCl_3$, DMF, THF, MeOH, IPA | No |
| Oxalic acid | 1:2 | Suspension | ACN, IPA, THF | No |
| L-tartaric acid | 1:1 | Wet milling | $H_2O$, $CHCl_3$, DMF, THF, MeOH, IPA | No |
| L-tartaric acid | 1:1 | Suspension | THF e CHCl3 | No |
| L-tartaric acid | 1:2 | Suspension | MeOH e THF | No |
| L + D tartaric acid | 1:1 | Wet milling | $H_2O$, $CHCl_3$, DMF, THF, MeOH, IPA | No |
| Propyl Gallate | 1:1 | Wet milling | $H_2O$, $CHCl_3$, DMF, THF, MeOH, IPA | No |
| Nicotinamide | 1:1 | Wet milling | $H_2O$, $CHCl_3$, DMF, THF, MeOH, IPA | No |
| Nicotinamide | 1:2 | Suspension | MeOH, acetone, dioxane, IPA | No |
| Gentisic Acid | 1:1 | Wet milling | $H_2O$, $CHCl_3$, DMF, THF, MeOH, IPA | Co-crystal Form 1 |
| Gentisic Acid | 1:2 | Wet milling | H2O | Co-crystal Form 1 + AG |
| Gentisic Acid | 2:1 | Wet milling | H2O | Co-crystal Form 1 + PMD |
| Gentisic Acid | 1:2 | Suspension | ACN, MIK e AcOiBu | No |
| Vanillic Acid | 1:1 | Wet milling | $H_2O$, $CHCl_3$, DMF, THF, MeOH, IPA | No |
| Vanillic Acid | 1:1 | Wet milling + seeding co-crystal Form 1 | $H_2O$, $CHCl_3$, DMF, THF, MeOH, IPA | No |
| Fumaric Acid | 1:1 | Wet milling | $H_2O$, $CHCl_3$, DMF, THF, MeOH, IPA | No |
| Saccharin | 1:1 | Wet milling | $H_2O$, $CHCl_3$, DMF, THF, MeOH, IPA | No |

TABLE 6-continued

| Co-former | R mol (PMD/AG) | Method | Solvents | Result |
|---|---|---|---|---|
| Nicotinic Acid | 1:1 | Wet milling | $H_2O$, $CHCl_3$, DMF, THF, MeOH, IPA | No |
| Ascorbic Acid | 1:1 | Wet milling | $H_2O$, $CHCl_3$, DMF, THF, MeOH, IPA | No |
| Benzoic Acid | 1:1 | Wet milling | $H_2O$, $CHCl_3$, DMF, THF, MeOH, IPA | No |
| Piridoxine | 1:1 | Wet milling | $H_2O$, $CHCl_3$, DMF, THF, MeOH, IPA | No |
| Piridoxine + HCl aq. | 1:1 | Wet milling | $H_2O$, $CHCl_3$, DMF, THF, MeOH, IPA | No |
| L-Piroglutamic Acid | 1:1 | Wet milling | $H_2O$, $CHCl_3$, DMF, THF, MeOH, IPA | No |
| L-malic Acid | 1:1 | Wet milling | $H_2O$, $CHCl_3$, DMF, THF, MeOH, IPA | No |
| 4-aminobenzoic Acid | 1:1 | Wet milling | $H_2O$, $CHCl_3$, DMF, THF, MeOH, IPA | No |
| L-Proline | 1:1 | Wet milling | $H_2O$, $CHCl_3$, DMF, THF, MeOH, IPA | No |
| Vanillin | 1:1 | Wet milling | $H_2O$, $CHCl_3$, DMF, THF, MeOH, IPA | No |
| Glycolic Acid | 1:1 | Wet milling | $H_2O$, $CHCl_3$, DMF, THF, MeOH, IPA | No |
| Sorbic Acid | 1:1 | Wet milling | $H_2O$, $CHCl_3$, DMF, THF, MeOH, IPA | No |
| Betaine | 1:1 | Wet milling | $H_2O$, $CHCl_3$, DMF, THF, MeOH, IPA | No |
| Cinnamic Acid | 1:1 | Wet milling | $H_2O$, $CHCl_3$, DMF, THF, MeOH, IPA | No |
| L-Glutamic Acid | 1:1 | Wet milling | $H_2O$, $CHCl_3$, DMF, THF, MeOH, IPA | No |
| 2,4-dihydroxy benzoic acid | 1:1 | Wet milling | $H_2O$, $CHCl_3$, DMF, THF, MeOH, IPA | No |
| 2,4-dihydroxy benzoic acid | 1:1 | Wet milling + seeding co-crystal Form 1 | $H_2O$, $CHCl_3$, DMF, THF, MeOH, IPA | No |
| 2,4-dihydroxy benzoic acid | 2:1 | Wet milling | DMF | No |
| 2,4-dihydroxy benzoic acid | 1:2 | Wet milling | DMF | No |
| Choline hydrochloride | 1:1 | Wet milling | $H_2O$, $CHCl_3$, DMF, THF, MeOH, IPA | No |
| Maltol | 1:1 | Wet milling | $H_2O$, $CHCl_3$, DMF, THF, MeOH, IPA | No |
| Formic Acid | 1:1.5 | Wet milling | $H_2O$, $CHCl_3$, DMF, THF, MeOH, IPA | No |

Abbreviations:
$H_2O$ water;
$CHCl_3$ chloroform;
DMF dimethylformamide;
THF tetrahydrofuran;
MeOH methanol;
IPA isopropanol;
ACN acetonitrile;
MIK methyl isobutyl ketone;
AcOiBu isobutyl acetate;
AG Gentisic acid;
PMD Pomalidomide.

Milling conditions: 0.5 ml solvent for 3 hours at room T.

Suspension conditions: 0.5 ml of solvent, under stirring for 5 hours at room T.

The final products were analyzed by XRPD.

From this screening only one co-crystal resulted, obtained by milling in the absence of seeding, the Pomalidomide: Gentisic acid (1:1) of the present invention.

From the table it is clearly seen that co-formers such as vanillic acid and 2,4-dihydroxybenzoic acid, although very similar to Gentisic acid, and others, for example urea, oxalic acid, DL-tartaric acid and propyl gallate although suitable to form co-crystals with the analogous Lenalidomide, did not lead to the desired co-crystal.

From the wet milling tests in water with various ratios of Gentisic acid with respect to Pomalidomide (1:2, 1:1, 2:1) it is confirmed that the ratio in the co-crystal is 1:1, because in the XRPD diffractograms the signals of Gentisic acid or Pomalidomide are visible when used in a molar excess with respect to the stoichiometric.

The co-crystal Pomalidomide: Gentisic acid (1:1) according to the present invention was obtained from different solvents ($H_2O$, $CHCl_3$, DMF, THF, MeOH, IPA) and therefore it would not be a solvated or hydrated form, as also confirmed by TGA.

Example 6

Preparation Screening of Form 1 Co-Crystal Pomalidomide: Gentisic Acid 1:1 by Suspension in Solvent Several formation tests of the present co-crystal have been performed by suspension of Pomalidomide and Gentisic acid at different molar ratios, in various solvents, under stirring at room temperature overnight, seeding with crystals of the co-crystal Pomalidomide: Gentisic acid Form 1, obtained as described in Example 5, in particular under the operating conditions reported in the following table 7:

TABLE 7

| Molar ratio Pomalidomide/Gentisic acid | Solvent | Result (XRPD) |
|---|---|---|
| 1:1 | H₂O | Co-Crystal Form 1 + Pomalidomide |
| 1:2 | IPA | Pomalidomide + Gentisic Acid |
| 1:4 | IPA | Pomalidomide + Gentisic Acid |
| 1:2 | ACN | Co-Crystal Form 1 |
| 1:4 | AcOiBu | Co-Crystal Form 1 + Pomalidomide |

The results of this screening highlight acetonitrile as preferred solvent for the preparation in suspension of the present pure co-crystal, while the preliminary tests from water and AcOiBu have led to an only partial conversion of Pomalidomide even in excess of Gentisic acid.

Example 7

Preparation of the Co-Crystal Pomalidomide: Gentisic Acid 1:1 Form 1 by Suspension in Acetonitrile Pomalidomide (Form O, example 1, 150 mg, 0.55 mmol) and Gentisic acid (169 mg, 1.1 mmol, 2 eq.) were introduced into a test tube equipped with magnetic stirring. Acetonitrile was added (1 ml, 6.7 vol.), the resulting mixture was seeded with Form 1 and stirred at room temperature overnight.

The solid was filtered with a sintered glass filter (No. 3) and washed with ACN (2×2 vol, 2×0.3 ml). After vacuum drying at room temperature, 232 mg were obtained of pure Form 1 co-crystal Pomalidomide: Gentisic acid as a white solid (yield 99%).

Characterization of Form 1 of the Co-Crystal Pomalidomide: Gentisic Acid (1:1)

The Form 1 co-crystal Pomalidomide: Ac Gentisic prepared in Example 7, was characterized by ¹H-NMR, XRPD, DSC and TGA.

¹H-NMR (DMSO-d6)

The ¹H-NMR spectrum of the sample of Form 1 (FIG. 3) resulted the exact superposition of the spectra of Pomalidomide Form O and Gentisic acid. Neither degradation nor signal shifts were observed. The ratio between the signals confirmed the 1:1 ratio of the components in the co-crystal deduced from the wet milling experiments. Acetonitrile was not present.

XRPD

The XRPD analysis of the co-crystal Form 1 was performed (FIG. 8). In the following table 8, the peaks with relative intensity higher than or equal to 1% have been reported:

TABLE 8

| Pos. [°2Th.] | d-spacing [Å] | Rel. Int. [%] |
|---|---|---|
| 7.1 | 12.5 | 14 |
| 8.0 | 11.0 | 3 |
| 10.5 | 8.4 | 15 |
| 10.9 | 8.1 | 73 |
| 12.7 | 7.0 | 27 |
| 13.7 | 6.4 | 89 |
| 14.2 | 6.2 | 100 |
| 14.6 | 6.1 | 47 |

TABLE 8-continued

| Pos. [°2Th.] | d-spacing [Å] | Rel. Int. [%] |
|---|---|---|
| 15.6 | 5.7 | 28 |
| 16.1 | 5.5 | 43 |
| 16.6 | 5.3 | 51 |
| 17.4 | 5.1 | 26 |
| 17.7 | 5.0 | 30 |
| 17.9 | 5.0 | 24 |
| 18.6 | 4.8 | 7 |
| 19.1 | 4.6 | 23 |
| 19.5 | 4.5 | 12 |
| 20.2 | 4.4 | 34 |
| 21.2 | 4.2 | 29 |
| 21.5 | 4.1 | 77 |
| 21.9 | 4.1 | 14 |
| 22.6 | 3.9 | 11 |
| 23.1 | 3.8 | 10 |
| 23.9 | 3.7 | 10 |
| 24.4 | 3.6 | 6 |
| 25.2 | 3.5 | 50 |
| 25.3 | 3.5 | 64 |
| 26.0 | 3.4 | 81 |
| 26.4 | 3.4 | 26 |
| 26.8 | 3.3 | 24 |
| 27.4 | 3.2 | 18 |
| 28.0 | 3.2 | 6 |
| 28.6 | 3.1 | 48 |
| 29.5 | 3.0 | 6 |
| 30.2 | 3.0 | 6 |
| 30.8 | 2.9 | 5 |
| 31.5 | 2.8 | 6 |
| 31.7 | 2.8 | 6 |
| 32.2 | 2.8 | 6 |
| 32.6 | 2.7 | 13 |
| 32.9 | 2.7 | 14 |
| 33.8 | 2.7 | 6 |
| 33.7 | 2.7 | 8 |
| 34.8 | 2.6 | 1 |
| 35.7 | 2.5 | 1 |
| 36.4 | 2.5 | 3 |
| 37.2 | 2.4 | 1 |
| 38.3 | 2.3 | 4 |
| 38.9 | 2.3 | 7 |
| 39.5 | 2.3 | 2 |

DSC

The co-crystal Form 1 is characterized by an endothermic peak starting at 226° C. (melting enthalpy ~271.93 J/g) and peak at about 232° C., corresponding to the melting and degradation of the Form 1, measured by DSC analysis (10° C./min) (FIG. 5).

TGA

The thermogravimetric analysis of the co-crystal Form 1 showed only a negligible weight loss before the melting point (FIG. 6). Therefore, the co-crystal Form 1 does not appear to be a hydrate. The thermal event after the melting point would correspond to decomposition.

Example 8

Preparation of the Co-Crystal Pomalidomide: Gentisic Acid Form 1 by Suspension in Water 3.55 g (12.99 mmol) of Pomalidomide Form O (example 1), 3.00 g (19.46 mmol, 1.5 eq.) of Gentisic acid and water (35 ml) were introduced into a 100 ml three necked flask equipped with mechanical stirring and thermometer. The mixture was heated to 50° C., under stirring, seeded with crystals of co-crystal Form 1 and monitored by XRPD.

After 6.5 hours of stirring at 50° C. there was complete conversion. The solid was filtered at 50° C. with a sintered filter (No. 2) and washed with water at 50° C. (2×7 ml). After drying at room temperature and at atmospheric pressure, and thereafter at 50° C. under vacuum to constant weight, 5.24 g of co-crystal Pomalidomide: Gentisic acid Form 1 as a yellow solid were obtained (yield 95%).

Characterization of Co-Crystal Pomalidomide: Gentisic Acid (1:1) Form 1

The $^1$H-NMR spectrum of the present co-crystal Form 1 was corresponding to the reference spectrum of FIG. 3. The ratio of the components in the co-crystal was 1:1.

A sample of the present co-crystal Form 1 has been subjected to XRPD analysis. The diffractogram proved corresponding to the reference of the FIG. 8.

Water Content (Karl Fischer)

The water content analysis according to Karl Fischer has been carried out using the instrument Metrohm 787 KF Trinito. Three samples of co-crystal Pomalidomide: Gentisic acid Form 1 of Example 8, of weight 49.5 mg, 51 mg and 49.1 mg were analyzed with the following reagents: Hydranal-Composite 5 (Riedel de Haen Ref. 34081) Hydranal Methanol Rapad (Riedel de Haen Ref. 37817) and Hydranal water Standard 10.0 (Riedel de Haen Ref. 34849 used to calculate the factor). According to these analyzes, the samples showed a very low average water content, i.e. equal to 0.82% (average of three analyzes), although they had been prepared from water, confirming the fact that the co-crystal was not a hydrated form.

Example 9

The following batches of crude Pomalidomide Form A and of co-crystal Pomalidomide: Gentisic acid:

Lot A: 2.5 g Crude Pomalidomide,

Lot B: 5 g Crude Pomalidomide, prepared as described in patent application WO2007005972, and Lot C: 10 g Co-Crystal Form 1 of Pomalidomide: Gentisic acid, prepared as in Example 7 above, were used for the studies reported hereinafter.

Solubility and Stability in Solution of the Co-Crystal of Pomalidomide: Gentisic Acid Form 1

A comparative study of solubility of the co-crystal Form 1 Lot C in relation to Pomalidomide Lot A in aqueous solutions has been performed, with the following operating conditions:

Temperature: room temperature (24° C.) and 37° C.;

Buffer solutions: pH 1.2 (hydrochloric acid) and pH 6.8 (phosphate buffer)

The solutions were prepared as described in the US Pharmacopoeia USP 35 NF 30. However, in the case of phosphate buffer (pH 6.8) more concentrated solutions were used, in order to increase the strength of the buffer and maintain a constant pH despite the release of high amounts of Gentisic acid from the co-crystal Form 1.

Samples were taken at different times (0.5 h, 1 h, 3 h and 24 h).

The relative solubility of Pomalidomide over time has been evaluated, at different pH and temperatures, comparing the areas of the Pomalidomide HPLC peaks of samples taken from the filtrate of the Pomalidomide crystal dispersions Lot A and co-Crystal Form 1 Lot C.

Experimental Procedure

The solubility of Pomalidomide (PMD) and of its co-crystal with Gentisic acid (Form 1) were measured in particular at the following operating conditions of pH and temperature:

pH 1.2 (hydrochloric acid) at room temperature (24° C.);

pH 1.2 (hydrochloric acid) 37° C.;

pH 6.8 (phosphate buffer) 37° C.

For each operating condition, the solubility study has been performed for co-Crystal Form 1 Lot C and for Pomalidomide Lot A in duplicate (for a total of 12 solubility measures).

The co-crystal form 1 and Pomalidomide were pulverized in a mortar. 200 mg of each product were then stirred in the corresponding aqueous buffer solution (24 ml, 120 vol) under the same conditions of stirring speed (900 rpm stirring with magnetic stir bar 2 cm long) and in the same type of flask (50 ml round-bottomed flask).

Aliquots of about 6 ml of the suspension were taken and filtered at different times: (at 30, 60, 180 min and 24 h). After filtration, the mother liquors were directly analyzed by HPLC (performing 2 replicates for each analysis) and their pH was measured.

The filtered solid was analyzed by XRPD, without a drying stage. These analyzes, in the case of the co-crystal Form 1, indicate if the measured solubility corresponds to the co-Crystal Form 1 only, to a mixture of re-precipitated Pomalidomide with the co-crystal Form 1 or to precipitated Pomalidomide only.

To determine the solubility of Pomalidomide the following HPLC operating conditions were chosen:

Column: Zorbax Eclipse C18 (XDB), 150×4.6 mm 5 micron

Sample concentration: 0.5 mg/ml ACN:H2O:H3PO4 (65:35:0.2 v/v)

Mobile phase: A: ACN:H2O:H3PO4 (5:95:0.1 v/v; B: ACN; (A/B 85/15)

Temperature: room temperature

Flow rate: 1 ml/min

UV detector (wavelength): 225 nm

Injection: 5 ml

Acquisition time: 12 min

Solubility at pH 1.2 and at Room Temperature

Figure 16:
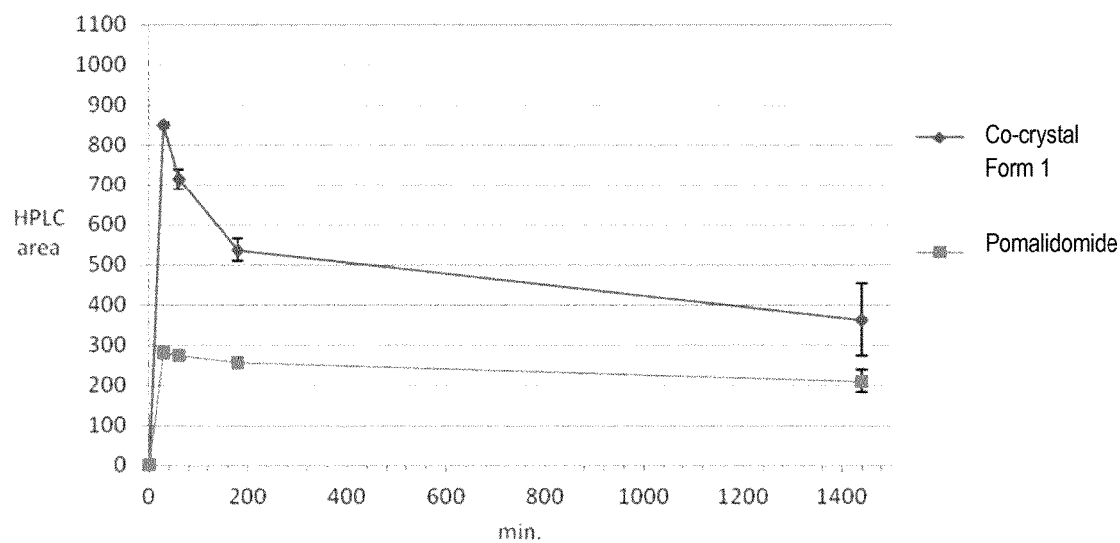
FIG. 16 is a graph that reports the results of solubility studies at room temperature in a buffer solution at pH 1.2 of Pomalidomide and of its co-crystal Form 1.

The results of the solubility studies at room temperature (about 24° C.) of samples obtained by dissolving Pomalidomide and its co-Crystal Form 1, respectively, in a buffer solution at pH 1.2 have been reported in the diagram of FIG. 16 as average of the HPLC area values of Pomalidomide (PMD) against time.

From the diagram, an improvement in solubility is clearly visible, particularly high during the first 3 hours (by a factor of 3 or 4 times), for the co-crystal Form 1. Subsequently, the solubility decreases gradually but anyhow remaining at higher values than those of the crystalline Pomalidomide even after 24 h.

By XRPD analysis, it has been possible to follow the dissociation of the co-crystal Form 1: a partial dissociation was observed at 30 min and the complete dissociation after 24 h.

Solubility at pH 1.2 and 37° C.

Figure 17:
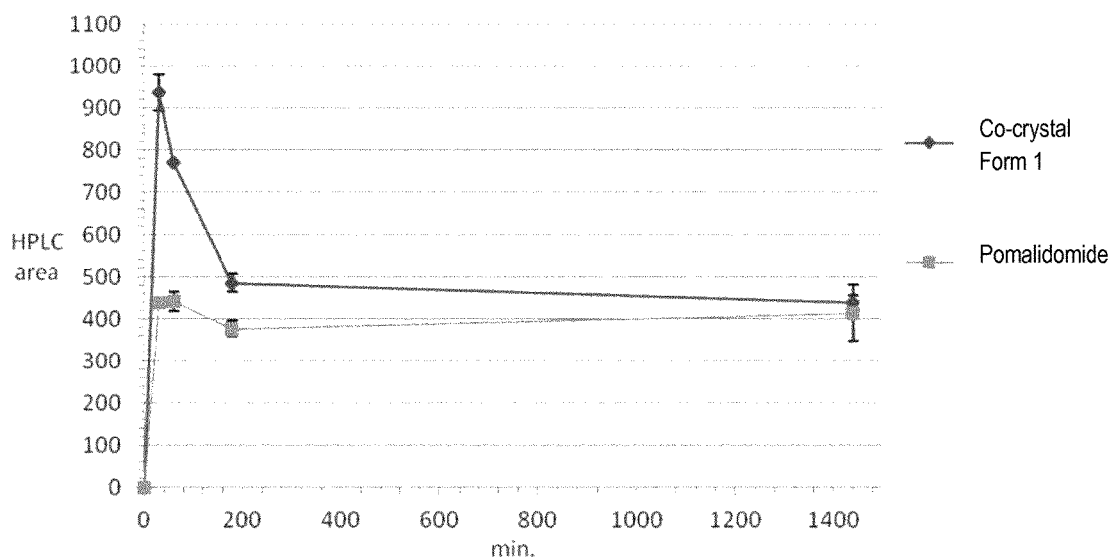
FIG. 17 is a graph that reports the results of solubility studies at 37° C. in a buffer solution at pH 1.2 of Pomalidomide and of its co-crystal Form 1.

The results of solubility studies at 37° C. in buffer solution at pH 1.2 are shown in the diagram of FIG. 17.

As in the case of the experimentation performed at 24° C., a significantly higher solubility of the co-crystal Form 1 was observed in the first hours with respect to Pomalidomide crystals.

By XRPD analysis, it was observed that the dissociation of Form 1 is faster at 37° C. than at 24° C., and is complete after only 3 hours.

Solubility at pH 6.8 and at Room Temperature

The solubility studies of the co-crystal of Form 1 and of Pomalidomide in a buffer solution at pH about 6.8 (phosphate buffer) were performed in duplicate. The buffer solution was prepared in a manner similar to that described in USP 35-NF 30, but at higher concentrations (0.15 M instead of 0.05 M) in order to maintain the buffering effect (the pH of the buffer solution 0.05M decreased from 6.8 to 5.8 when the co-crystal Form 1 was used).

Figure 18:
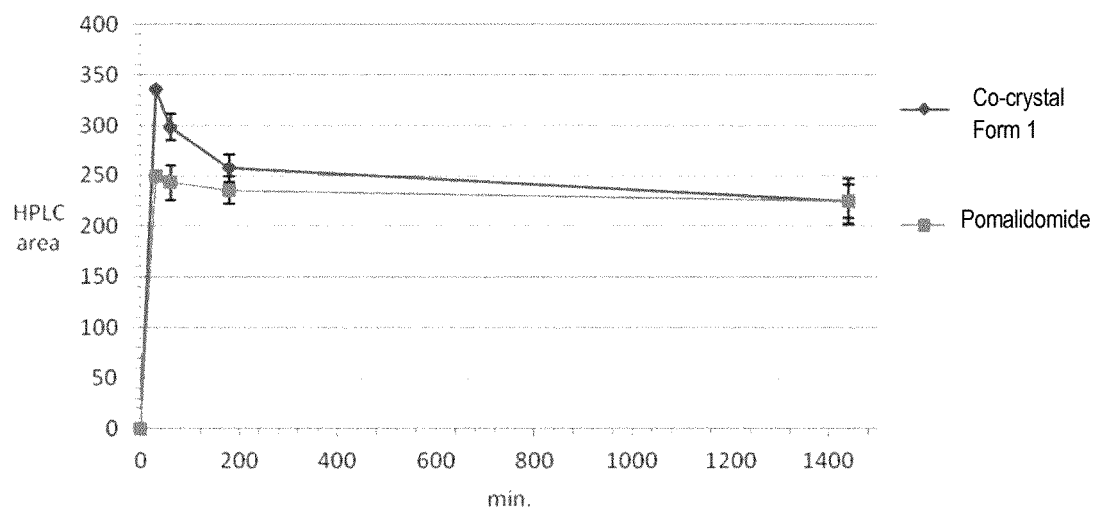
FIG. 18 is a graph that reports the results of solubility studies at room temperature in a buffer solution at pH 6.8 of Pomalidomide and its co-crystal Form 1.

The results of solubility studies at room temperature (about 24° C.) in a buffered solution at pH 6.8 are shown in the FIG. 18 diagram.

As in previous experiments, a better solubility was observed for the co-crystal Form 1 with respect to Pomalidomide during the first hour (by a factor of 1.2 to 1.4 times), then the solubility decreased gradually until reaching the solubility of crystalline Pomalidomide after 24 h.

By XRPD analysis, it could be observed that the dissociation of the co-crystal Form 1 was complete after 30 minutes.

In conclusion the above tests show that the co-crystal Pomalidomide: Gentisic acid Form 1 has a better water solubility than Pomalidomide.

Example 10

Analytical Characterization of the Impurities

Two samples for each batch A and B of Pomalidomide Form A (crude) and C of co-crystal Pomalidomide: Gentisic acid were analyzed by HPLC under the previously described operating conditions. The average values (area %) and the respective retention times (RT) of the products and of the main impurities are shown in the following Table 9:

TABLE 9

| Lot | AG RT 4.2 min | Impurity 1 RT 6.0 min | PMD RT 9.2 min | Impurity 2 RT 10.4 min | Impurity 3 RT 11 min |
|---|---|---|---|---|---|
| A | — | 0.05 | 99.6 | 0.08 | 0.12 |
| B | — | 0.10 | 98.6 | 0.12 | 1.06 |
| C | 25.4 | 0.02 | 74.2 | 0.12 | 0.01 |

AG Gentisic acid PMD Pomalidomide RT retention time

Purification Pomalidomide Via Co-Crystal

Pomalidomide lot B, containing the largest amount of impurities, was used as starting material in the following purification tests through formation of the co-crystal with Gentisic acid Form 1 by suspension in a solvent (slurrying), under the operating conditions shown in the following Table 10:

TABLE 10

| Ex. | Operating Conditions | AG area % | Imp. 1 area % | PMD area % | Imp. 2 area % | Imp. 3 area % | Yield |
|---|---|---|---|---|---|---|---|
| 10a | H₂0 50° C. 200 mg PMD: 1.5 eq. AG | 26.0% | 0.06 (0.08) | 73.1 (98.8) | 0.07 (0.09) | 0.72 (0.97) | 96% |
| 10b | ACN 50° C. 200 mg PMD: 2 eq. AG | 25.5% | 0.07 (0.09) | 73.8 (99.1) | 0.06 (0.08) | 0.47 (0.63) | 98% |
| 10c | ACN T. Amb. 200 mg PMD: 2 eq. AG | 27.2% | 0.06 (0.08) | 72.1 (99.0) | 0.06 (0.08) | 0.48 (0.66) | 94% |
| B | — | — | 0.10 | 98.6 | 0.12 | 1.06 | — |

Abbreviations:
B crude Pomalidomide Lot B;
AG Gentisic acid;
PMD Pomalidomide;
Imp. Impurity;
Eq. equivalent;
ACN acetonitrile T. Amb. Room temperature.

The values given in parentheses represent percent areas calculated by excluding the area of the Gentisic acid peak.

As it can be seen from the data reported in the above table, the best purification effect was observed with hot acetonitrile (example 10b), in particular with respect to the impurity 3 that is reduced from 1.06% to 0.66%. The Pomalidomide B, thanks to the process of purification of examples 10b and 10c advantageously achieves a purity of 99% and higher.

To confirm the effectiveness of the purification of Pomalidomide via co-crystal, the preparation of the co-crystal Form 1 in ACN at 50° C. was repeated on a larger scale (example 10d in the following table 11). A blank test was also performed (1 suspension of crude Pomalidomide in ACN at 50° C. without Gentisic acid example 10e in the table 11) to confirm that the purification actually depends on the formation of the co-crystal form 1 and not simply on the purifying effect of the solvent on the crude in suspension under stirring (slurrying). The operating conditions of the tests and the results of the HPLC analysis conducted on these samples are reported in the following Table 11:

TABLE 11

| Ex. | Operating Conditions | AG area % | Imp. 1 area % | PMD area % | Imp. 2 area % | Imp. 3 area % | Yield |
|---|---|---|---|---|---|---|---|
| B | — | — | 0.10 | 98.6 | 0.12 | 1.06 | — |
| 10d | ACN, 50° C. 700 mg of PMD: 2 eq. AG | 24.0 | 0.07 (0.09) | 75.2 (98.9) | 0.10 (0.13) | 0.50 (0.66) | 91% |
| 10e | ACN, 50° C. | — | 0.04 | 98.8 | 0.12 | 0.89 | — |

As it can be seen, the product obtained in example 10e, compared with the crude B, shows only a slight reduction of the impurity content, in particular a negligible decrease of the impurity 3 which is instead definitely lower in example 10d according to the invention.

In the following example 10f the co-crystal Pomalidomide: Gentisic acid was prepared increasing the amount of the latter from 2 to 3 equivalents, in order to obtain a more complete conversion of Pomalidomide, as shown in Table 12:

TABLE 12

| Ex. | Operating Conditions | AG area % | Imp. 1 area % | PMD area % | Imp. 2 area % | Imp. 3 area % | Yield |
|---|---|---|---|---|---|---|---|
| B | — | — | 0.10 | 98.6 | 0.12 | 1.06 | — |
| 10f | ACN, 50° C. 500 mg PMD: 3 eq. AG | 27.1 | 0.05 (0.07) | 72.5 (99.5) | 0.02 (0.03) | 0.31 (0.43) | 93% |

In the following experiments, the purification process has been repeated via co-crystal, preparing the co-crystal in acetonitrile, dissociating the co-crystal thus obtained in example 10f by suspension in acetone under stirring (slurrying), recovering Pomalidomide by filtration (example 10g) and preparing the co-crystal again in acetonitrile (example 10h), as schematically shown in the following Table 13:

TABLE 13

| Ex. | Operating Conditions | AG area % | Imp. 1 area % | PMD area % | Imp. 2 area % | Imp. 3 area % | Yield |
|---|---|---|---|---|---|---|---|
| B | — | — | 0.10 | 98.6 | 0.12 | 1.06 | — |
| 10g | Sample 10f in acetone (10 vol) | 0.01 | 0.08 | 99.4 | 0.05 | 0.43 | 96% |
| 10h | ACN, 50° C. 100 mg PMD from ex. 10g; 3 eq. AG | 26.2 (—) | 0.05 (0.07) | 73.6 (99.7) | 0.04 (0.05) | 0.14 (0.19) | 90% |

As evidenced by the data reported in Table 13, repeating twice the co-crystallization process, Pomalidomide was obtained with an even higher degree of purity (from 98.6% initial to 99.7%), particularly advantageous for a pharmaceutical ingredient. After the second co-crystallization the impurity 3 is reduced from 1.06% to 0.14%. Advantageously, the solvent used in the crystallization of the 10 h sample, acetonitrile, is quite volatile and can be easily removed from the final product.

Example 11

Pomalidomide Purification by Suspension Under Stirring of the Co-Crystal Form 1 in Various Solvents The effect of various solvents (ethyl acetate, methyl isobutyl ketone, ethanol, isopropanol and acetone) has been studied on the purity of Pomalidomide by suspension and stirring of the co-crystal Form 1.

Co-Crystal Form 1, prepared in ACN at 50° C. (example 10d *see Table 11), was suspended in 10 volumes of solvent and the resulting mixture stirred at room temperature for one night. The solid was filtered, washed with the same solvent (2×2 volumes) and dried under vacuum at room temperature. The chemical purity of Pomalidomide has been checked after 3.5 hours and after a night (see the following Table 14). A sample of each product was analyzed by HPLC in duplicate. In all solvents, after 3.5 hours, the co-crystal has been shown to be dissociated (as confirmed by XRPD).

TABLE 14

| Ex. | Operating Conditions | AG area % | Imp. 1 area % | PMD area % | Imp. 2 area % | Imp. 3 area % |
|---|---|---|---|---|---|---|
| 10d | — | 24.0 | 0.07 (0.09) | 75.2 (98.9) | 0.10 (0.13) | 0.50 (0.66) |
| 11a | 10d (Form 1) EtOAc, 3.5 h | 0.10 | 0.10 | 98.9 | 0.28 | 0.61 |
| 11b | 10d (Form 1) EtOAc, night | 0.23 | 0.09 | 98.8 | 0.20 | 0.62 |
| 11c | 10d (Form 1) MIBK, 3.5 h | 0.11 | 0.10 | 98.9 | 0.22 | 0.62 |
| 11d | 10d (Form 1) MIBK, night | 0.98 | 0.09 | 98.0 | 0.24 | 0.62 |
| 11e | 10d (Form 1) EtOH, 3.5 h | 0.25 | 0.10 | 98.8 | 0.23 | 0.61 |
| 11f | 10d (Form 1) EtOH, night | 0.53 | 0.10 | 97.4 | 0.24 | 0.62 |
| 11g | 10d (Form 1) IPA, 3.5 h | 0.31 | 0.10 | 98.8 | 0.20 | 0.62 |
| 11h | 10d (Form 1) IPA, night | 0.11 | 0.10 | 99.0 | 0.19 | 0.57 |
| 11i | 10d (Form 1) Acetone, 3.5 h | 0.25 | 0.10 | 98.8 | 0.22 | 0.58 |
| 11l | 10d (Form 1) Acetone, night | 0.39 | 0.10 | 98.6 | 0.20 | 0.63 |

As it can be seen from the data shown in Table 14, the tested solvents (EtOAc, MIBK, EtOH, IPA and acetone) have not led to a significant decrease of the impurities after 3.5 h, not even after one night. These data further confirm that the purification of Pomalidomide is attributable to the formation and crystallization of the co-crystal Form 1 and not to the effect of the solvent itself in simple conditions of slurrying.

Example 12

Hygroscopicity of the Co-Crystal Pomalidomide: Gentisic Acid Form 1

A DVS study (Dynamic Vapour Sorption, dynamic absorption of vapour) was performed to evaluate the hygroscopicity of the co-crystal Pomalidomide: Gentisic acid Form 1 in a wide range of relative humidities (RH).

The hygroscopicity of the co-crystal was determined by DVS with a TA Q5000 instrument. The DVS is a gravimetric technique that measures the amount of water absorbed or desorbed by a sample under different relative humidity conditions. The change in mass is measured at predetermined values of relative humidity (RH).

Figure 15:
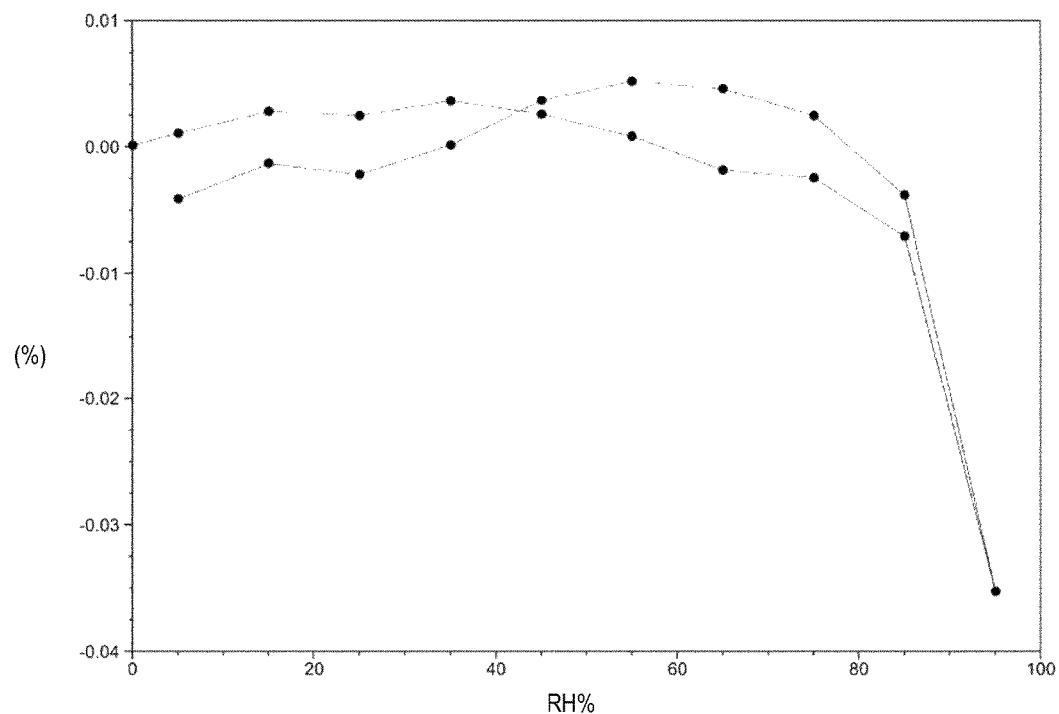
FIG. 15 is a thermogravimetric diagram concerning the Dynamic Vapor Sorption (DVS) of the co-crystal Pomalidomide: Gentisic acid Form 1.

Absorption and desorption isotherms were carried out at 25° C. in a range of 0 to 95% RH, and the results are reported in the diagram of FIG. 15.

In particular a DVS analysis was performed with 13.2922 mg of Form 1 Lot C in the following operating conditions:

Gravimetric Equilibration at 25° C. and 0% RH
Before moving on to the next level of humidity, the gravimetric variation had to be less than 0.01% for 20 minutes or else up to a maximum time of 300 min was waited.

From FIG. 15 it appears that the Form 1 of the co-crystal of Pomalidomide: Gentisic acid according to the invention is non-hygroscopic because between 0% and 95% RH no significant absorption of moisture occurred.

In order to confirm that the form 1 of the co-crystal is not converted to another crystal form by exposure to high relative humidity, a sample of Form 1 has been stored at room temperature at 95% relative humidity for 1 week. By XRPD, there were no major crystal transformations.

The invention claimed is:

1. Solid crystal form of Pomalidomide which is a co-crystal of Pomalidomide and Gentisic acid wherein:
   the molar ratio between Pomalidomide and Gentisic acid is 1:1, and
   the co-crystal is characterized by an endothermic melting peak at about 232° C. (DSC).

2. The co-crystal according to claim 1 wherein the co-crystal is further characterized by a XRPD diffractogram having at least the peaks 2θ (°) at 13.7, 14.2, and 26.0±1%.

3. The co-crystal according to claim 1 wherein the XRPD diffractogram is further characterized by peaks 2θ (°) at 10.9, 21.5, and 25.3±1%.

4. The co-crystal according to claim 1 wherein the XRPD diffractogram substantially corresponds to that shown in FIG. 8.

5. Process for the preparation of a co-crystal of Pomalidomide and Gentisic acid, comprising:
   a) providing Pomalidomide in a pre-established amount;
   b) providing Gentisic acid in a molar ratio of not more than 4:1, 3:1, 2:1, 1.5:1 or 1.2:1 compared to Pomalidomide;
   c) contacting Pomalidomide and Gentisic acid and, optionally, at least one Pomalidomide:Gentisic acid co-crystal:

c1) in solution or in suspension, in a suitable solvent, optionally selected from acetonitrile, water, isobutyl acetate and mixtures thereof, or
c2) by milling, optionally in the presence of traces of a suitable solvent, optionally selected from water, chloroform, dimethylformamide, tetrahydrofuran, methanol, isopropyl alcohol and mixtures thereof,
d) maintaining Pomalidomide and Gentisic acid in contact for a time necessary to form the co-crystal according to claim 2 and, optionally,
e) separating the co-crystal from the solvent, wherein:
the molar ratio between Pomalidomide and Gentisic acid is 1:1; and
the co-crystal is characterized by an endothermic melting peak at about 232° C. (DSC).

6. The process according to claim 5 wherein the Pomalidomide and Gentisic acid are contacted by suspension, optionally under stirring.

7. The process according to claim 6 wherein the volume of solvent relative to the weight of the Pomalidomide is less than 15 ml/g.

8. The process according to claim 5 wherein the Pomalidomide and Gentisic acid are contacted by milling, wherein the volume of solvent relative to the weight of the Pomalidomide is less than 10 ml/g.

9. A pharmaceutical composition comprising a therapeutically effective amount of a solid crystal form of Pomalidomide which is a co-crystal of Pomalidomide and Gentisic acid and at least one pharmaceutically acceptable excipient wherein:
the molar ratio between Pomalidomide and Gentisic acid is 1:1; and
the co-crystal is characterized by an endothermic melting peak at about 232° C. (DSC).

10. A method for the treatment of tumors, of multiple myeloma, comprising administering a solid crystal form of Pomalidomide which is a co-crystal of Pomalidomide and Gentisic acid, and mixtures thereof to a patient in need thereof wherein:
the molar ratio between Pomalidomide and Gentisic acid is 1:1; and
the co-crystal is characterized by an endothermic melting peak at about 232° C. (DSC).

11. Process for the purification of Pomalidomide comprising:
a) providing crude Pomalidomide in a predetermined amount;
b) providing Gentisic acid in a molar ratio of not more than 4:1, 3:1, 2:1, 1.5:1 or 1.2:1, with respect to Pomalidomide;
c) contacting crude Pomalidomide and Gentisic acid, in solution or in suspension in a suitable solvent, optionally selected from acetonitrile, water, isobutyl acetate and mixtures thereof, optionally in the presence of at least one Pomalidomide: Gentisic acid co-crystal;
d) maintaining Pomalidomide and Gentisic acid in contact for a time necessary to form the Pomalidomide: Gentisic acid co-crystal,
e) separating the obtained Pomalidomide: Gentisic acid co-crystal from the solvent,
f) optionally crystallizing the Pomalidomide: Gentisic acid co-crystal from a suitable solvent, and
g) recovering purified Pomalidomide from the co-crystal Pomalidomide: Gentisic acid, optionally by suspension in an appropriate solvent, wherein:
the molar ratio between Pomalidomide and Gentisic acid is 1:1; and
the co-crystal is characterized by an endothermic melting peak at about 232° C. (DSC).

12. The process according to claim 7, wherein the volume of solvent relative to the weight of the Pomalidomide is less than 10 ml/g.

13. The process according to claim 12, wherein the volume of solvent relative to the weight of the Pomalidomide is less than 8 ml/g.

14. The process according to claim 8, wherein the Pomalidomide and Gentisic acid are contacted by milling, wherein the volume of solvent relative to the weight of the Pomalidomide is less than 5 ml/g.

15. The process according to claim 14, wherein the Pomalidomide and Gentisic acid are contacted by milling, wherein the volume of solvent relative to the weight of the Pomalidomide is less than 2 ml/g.

16. The process according to claim 15, wherein the Pomalidomide and Gentisic acid are contacted by milling, wherein the volume of solvent relative to the weight of the Pomalidomide is less than 1 ml/g.

17. The process according to claim 16, wherein the Pomalidomide and Gentisic acid are contacted by milling, wherein the volume of solvent relative to the weight of the Pomalidomide is less than 0.5 ml/g.

* * * * *